US006503712B1

(12) United States Patent
Thukral

(10) Patent No.: US 6,503,712 B1
(45) Date of Patent: Jan. 7, 2003

(54) METHODS AND COMPOSITIONS FOR PREPARING A GENOMIC LIBRARY FOR KNOCKOUT TARGETING VECTORS

(75) Inventor: Sushil K. Thukral, Thousand Oaks, CA (US)

(73) Assignee: Amgen Inc., Thousand Oaks, CA (US)

(*) Notice: Subject to any disclaimer, the term of this patent is extended or adjusted under 35 U.S.C. 154(b) by 0 days.

(21) Appl. No.: 09/569,975

(22) Filed: May 10, 2000

(51) Int. Cl.$^7$ .......................... C12Q 1/68; C07H 21/02; C07H 21/04; C12N 15/74

(52) U.S. Cl. ........................... 435/6; 536/23.1; 935/80; 435/471; 435/481; 435/483; 435/488; 435/DIG. 23; 435/DIG. 47

(58) Field of Search ........................... 536/23.1; 435/6, 435/471, 481, 483, 488, DIG. 23, DIG. 47; 935/80

(56) References Cited

U.S. PATENT DOCUMENTS

| | | | |
|---|---|---|---|
| 4,710,465 A | 12/1987 | Weismann et al. | 435/91.1 |
| 5,530,178 A | 6/1996 | Mak | 800/2 |
| 5,547,862 A | 8/1996 | Meador et al. | 435/91.3 |
| 5,557,032 A | 9/1996 | Mak | 800/2 |
| 5,616,491 A | 4/1997 | Mak et al. | 435/354 |
| 5,625,122 A | 4/1997 | Mak | 800/2 |
| 5,714,667 A | 2/1998 | Waterhouse et al. | 800/2 |
| 5,907,079 A | 5/1999 | Mak et al. | 800/2 |
| 6,090,554 A | 7/2000 | Woychik et al. | 435/6 |
| 6,090,629 A | 7/2000 | Woychik | 435/472 |

FOREIGN PATENT DOCUMENTS

| | | |
|---|---|---|
| WO | WO 95/14769 A | 1/1995 |
| WO | WO 99/23238 | 5/1999 |
| WO | WO 99/23239 | 5/1999 |

OTHER PUBLICATIONS

Weilguny, Dietmar, et al. (1991) Gene, 99:47–54.*
Wattler, Sigrid, et al. (1999) BioTechniques, 26(6):1150–1160.*
Nehls, M., et al. (1994) BioTechniques, 17(4):770–775.*
Ausubel et al., (Eds.), in *Current Protocols in Molecular Biology*, Chapter 5, "Construction of Recombinant DNA Libraries," John Wiley & Sons, Inc. p. 5.0.1–5.11.2 (1987).
Barinaga, M., "Knockout Mice Offer First Animal Model for CF," *Science*, 257:1046–1047 (1992).
Baudin, A. et al., "A simple and efficient method for direct gene deletion in *Saccharomyces cerevisiae*," *Nucleic Acids Research*, 21(14):3329–3330 (1993).
Bittner et al., "Expression and Secretion Vectors for Yeast," *Methods in Enzymol.*, 153: 516–544 (1987).
Bollag, R.J. et al., "Homologous Recombination In Mammalian Cells," *Annu. Rev. Genet.*, 23:199–225 (1989).

Bradley, A. et al., "Embryo–Derived Stem Cells: A Tool For Elucidating The Developmental Genetics Of The Mouse," *Current Topics in Developmental Biology*, 20:357–371 (1986).
Chen, C. et al., "Abnormal Fear Response and Aggressive Behavior in Mutant Mice Deficient for α–Calcium–Calmodulin Kinase II," *Science*, 266:291–294 (1994).
Christianson, T.W. et al., "Multifunctional yeast high–copy–number shuttle vectors," *Gene*, 110:119–122 (1992).
Dorin, J.R. et al., "Successful targeting of the mouse cystic fibrosis transmembrane conductance regulator gene in embryonal stem cells," *Transgenic Research*, 1:101–105 (1992).
Eliceiri et al., "Stable integration and expression in mouse cells of yeast artificial chromosomes harboring human genes", *Proc. Natl. Acad. Sci.*, vol. 88:2179–2183 (Mar. 1991).
Geitz, R.D. et al., "High Efficiency Transformation with Lithium Acetate," In *Molecular Genetics of Yeast, A Practical Approach*, J.R. Jonston, Ed., pp. 121–134 (1995).
Gu, H. et al., "Deletion of a DNA Polymerase β Gene Segment in T Cells Using Cell Type–Specific Gene Targeting," *Science*, 265:103–106(1994).
Guthrie, C. et al., Eds. in *Methods in Enzymology: Guide to Yeast Genetics and Molecular Biology*, vol. 194, Academic Press, pp. 182–187, 239–251, 319–329, 373–388, and 389–398 (1991).
Hamer, R.E. et al., "Production of transgenic rabbits, sheep and pigs by microinjection," *Nature*, 315:680–683 (1985).
Hanks, M. et al., "Rescue of the En–1 Mutant Phenotype by Replacement of En–1 with En–2," *Science*, 269:679–682 (1995).
Hoffman, C.S. et al., "A ten–minute DNA preparation from yeast efficiently releases autonomous plasmids for transformation of *Escherichia coli*," *Gene*, 57:267–272 (1987).
Hogan, et al. in *Manipulating the Mouse Embryo: A Laboratory Manual*, Cold Spring Harbor Laboratory Press, Cold Spring Harbor New York, pp. 91–149, 153–197, and 247–267 (1986).
Joyner, A.L., (ed.) in *Gene Targeting: A Practical Approach*, IRL Press, Oxford University Press, New York, pp. 107–144 and 147–178 (1993).
Joyner, A.L. et al., "Production of a mutation in mouse En–2 gene by homologous recombination in embryonic stem cells," *Nature*, 338:153–156 (1989).

(List continued on next page.)

Primary Examiner—Joseph K. McKane
Assistant Examiner—Thomas Friend
(74) Attorney, Agent, or Firm—Marshall, Gerstein & Borun

(57) ABSTRACT

The present invention is directed to methods for producing gene targeting constructs by homologous recombination using mouse genomic libraries arrayed in yeast shuttle vectors. The invention is also directed to methods of using targeting constructs made by the methods to generate transgenic animals.

24 Claims, 6 Drawing Sheets

OTHER PUBLICATIONS

Khrebtukova et al., "Utilization of microhomologous recombination in yeast to generate targeting constructs for mammalian genes", *Mutation Research–Fundamental and Molecular Mechanisms of Mutagenesis*, vol. 401, No. 1–2:11–25 (Jun. 5, 1998).

Knudsen, C.M. et al., "Bax–Deficient Mice with Lymphoid Hyperplasia and Male Germ Cell Death," *Science*, 270:96–99 (1995).

Koller, B.H. et al., "Toward an animal model of cystic fibrosis: Targeted interruption of exon 10 of the cystic fibrosis transmembrane regulator gene in embryonic stem cells," *Proc. Natl. Acad. Sci., USA*, 88:10703–10734 (1991).

Lorenz, M.C. et al., "Gene disruption with PCR products in *Saccharomyces cerevisiae*," *Gene*, 158:113–117 (1995).

Luo, Y. et al., "A Novel Method for Monitoring *Mycobacterium bovis* BCG Trafficking with Recombinant BCG Expressing Green Fluorescent Protein," *Clinical Diagnostic Laboratory Immunology*, 3(6):761–768 (1996).

Lutz, C.T. et al., "Syrinx 2A: An improved λ phage vector designed for screening DNA libraries by recombination in vivo," *Proc. Natl. Sci., USA*, 84:4379–4383 (1987).

Manivasakam, P. et al., "Micro–homology mediated PCR targeting in *Saccharomyces cerevisiae*," *Nucleic Acids Research*, 23(14):2799–2800 (1995).

Mansour, S.L. et al., "Disruption of the proto–oncogene int–2 in mouse embryo–derived stem cells: a general strategy for targeting mutations to non–selectable genes," *Nature*, 336:348–352 (1988).

Marx, J., "Knocking Genes In Instead of Out," *Science*, 269:636 (1995).

Michaud, E.J. et al., "The embryonic lethality of homozygous lethal yellow mice ($A^y/A^y$) is associated with the disruption of a novel RNA–binding protein," *Genes & Development*, 7:1203–1213 (1993).

Oldenbburg, K.R. et al., "Recombination–mediated PCR––directed plasmid construction in vivo in yeast," *Nucleic Acids Research*, 25(2):451–452 (1997).

Orr–Weaver, T.L. et al., "Fungal Recombination," *Microbiological Reviews*, 49(1):33–58 (1985).

Robertson, E.J. (ed.) in *Teratocarcinomas and embryonic stem cells, a practical approach*, IRL Press, Washington D.C., pp. 113–181 (1987).

Sambrook et al., *Molecular Cloning: A Laboratory Manual*, section p. 1.19, 1.74–1.75, 2.6, 8.2–8.86, and 9.2–9.58 Cold Spring Harbor Laboratories, Cold SPring Harbor, N.Y. (1989).

Seed, B., "Purification of genomic sequences from bacteriophage libraries by recombination and selection in vivo," *Nucleic Acids Research*, 11(8):2427–2445 (1983).

Sikorski, R.S. et al., "A System of Shuttle Vectors and Yeast Host Strains Designed for Efficient Manipulation of DNA in *Saccharomyces cerevisiae*," *Genetics*, 122:19–27 (1989).

Silva, A.J. et al., "Deficient Hippocampal Long–Term Potentiation in α–Calcium–Calmodulin Kinase II Mutant Mice," *Science*, 257:201–206 (1992).

Snouwaert, J.N. et al., "An Animal Model for Cystic Fibrosis Made by Gene Targeting," *Science*, 257:1083–1088 (1992).

Soriano et al., "Targeted Disruption of the c–src Proto–Oncogene Leads to Osteopetrosis in Mice," *Cell*, 64:693–702 (1991).

Storck, T. et al., "Rapid construction in yeast of complex targeting vectors for gene manipulation in the mouse," *Nucleic Acids Research*, 24(22):4594–4596 (1996).

Tavtigian, S.V. et al., "The complete BRCA2 gene and mutations in chromosome 13q–linked kindreds," *Nature Genetics*, 12:333–337 (1996).

Thomas, K.R. et al., "Site–Directed Mutagenesis by Gene Targeting in Mouse Embryo–Derived Stem Cells," *Cell*, 51:503–512 (1987).

Travis, J. "Scoring a Technical Knockout in Mice," *Science*, 256:1392–1394 (1992).

Tsuzuki et al., "Embryonic stem cell gene targeting using bacteriophage lambda vectors generated by phage–plasmid recombination", *Nucleic Acids Research*, vol. 26(4):988–993 (Feb. 15, 1998).

Veis, D.J. et al., "Bcl–2–Deficient Mice Demonstrate Fulminant Lymphoid Apoptosis, Polycystic Kidneys, and Hypopigmented Hair," *Cell*, 75:229–240 (1993).

Wang, N. et al., "Impaired Energy Homeostasis in C/EBPα Knockout Mice," *Science*, 269:1108–1112 (1995).

* cited by examiner

*Flow chart of constructing and arraying mouse genomic library in the yeast-E coli shuttle vector*

*Flow chart of constructing mouse knock out vectors from pooled mouse genomic library by using yeast homologous recombination*

FIG. 3

1. PCR amplify selection cassette with fusion primers containing at least 40 bp homology to cDNA sequence at either end.

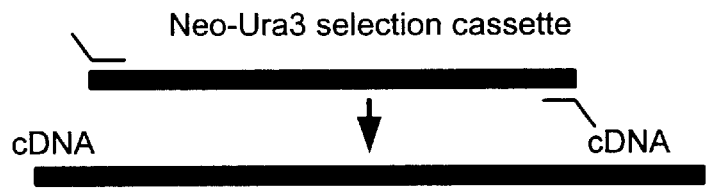

2. Recombination of cDNA-selection fusion cassette with genomic DNA fragments in yeast (genomic library in a yeast vector)

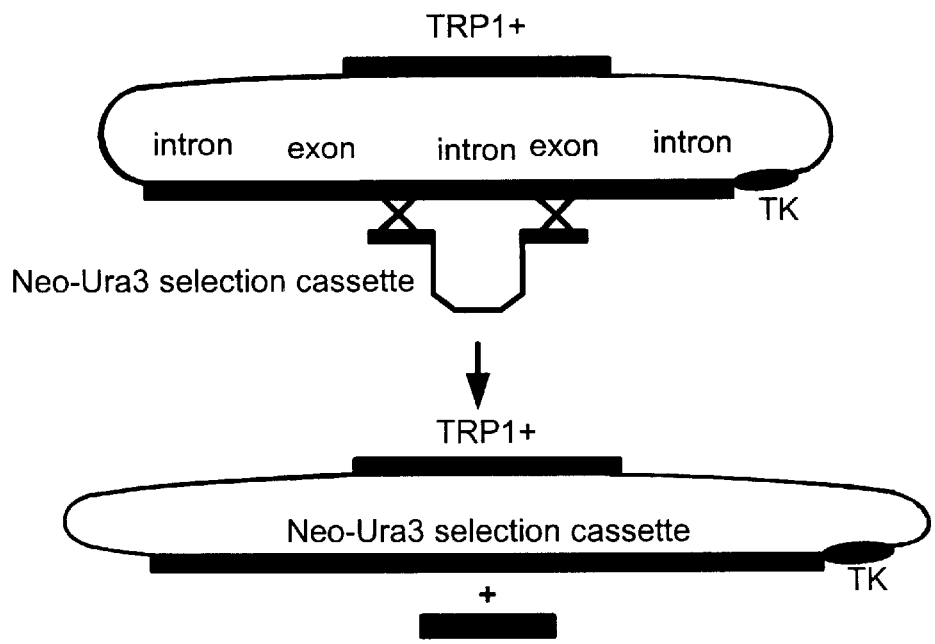

3. Growth selection for yeast transformants containing recombined cassette on trp- and ura-deficient medium

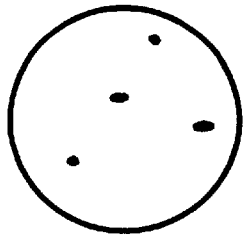

4. Rescue plasmid containing recombined knockout cassette from yeast to inject into mouse embryonic stem cells

SEQUENCE LISTING

```
<160> NUMBER OF SEQ ID NOS:  19

<210> SEQ ID NO 1
<211> LENGTH: 74
<212> TYPE: DNA
<213> ORGANISM: Artificial Sequence
<220> FEATURE:
<223> OTHER INFORMATION: Description of Artificial Sequence: primer

<400> SEQUENCE: 1
catttaggtg acactatagc ggccgcggat ccctatagtg agtcgtatta cggaccgtcg      60
acttaattaa catg                                                       74

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 2
gagcagttgg gctcagagg                                                  19

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: vector
      sequence

<400> SEQUENCE: 3
gtgatgctaa tgaacgagag ag                                              22

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 4
gtgctacttc catttgtcac g                                               21

<210> SEQ ID NO 5
<211> LENGTH: 21
```

```
<212> TYPE: DNA
<213> ORGANISM: Artificial Sequence
<220> FEATURE:
<223> OTHER INFORMATION: Description of Artificial Sequence: primer

<400> SEQUENCE: 5
agcagaattg tcatgcaagg g                                            21

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 6
gtagaagatg gatggcatga                                              20

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 7
cagctcatct gtcagatatt tc                                           22

<210> SEQ ID NO 8
<211> LENGTH: 65
<212> TYPE: DNA
<213> ORGANISM: Artificial Sequence
<220> FEATURE:
<223> OTHER INFORMATION: Description of Artificial Sequence: primer

<400> SEQUENCE: 8
ccttggagcc cctgaattgc attttgcagt agctcgaagg agaaacaagg cagtctggag   60
catgc                                                              65

<210> SEQ ID NO 9
<211> LENGTH: 70
<212> TYPE: DNA
<213> ORGANISM: Artificial Sequence
<220> FEATURE:
<223> OTHER INFORMATION: Description of Artificial Sequence: primer

<400> SEQUENCE: 9
tggaagacac ttacgtttta cttgttctgt tttgcttcct tctaggtgag tttagtatac   60
atgcatttac                                                         70

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 10
ggtctcagtg ttggaacagg a                                            21

<210> SEQ ID NO 11
<211> LENGTH: 21
<212> TYPE: DNA
<213> ORGANISM: Artificial Sequence
<220> FEATURE:
```

<223> OTHER INFORMATION: Description of Artificial Sequence: primer

<400> SEQUENCE: 11
gtacagttga gaagaggaaa g                                          21

<210> SEQ ID NO 12
<211> LENGTH: 74
<212> TYPE: DNA
<213> ORGANISM: Artificial Sequence
<220> FEATURE:
<223> OTHER INFORMATION: Description of Artificial Sequence: primer

<400> SEQUENCE: 12
ttaattaagt cgacggtccg taatacgact cactataggg atccgcggcc gctatagtgt   60
cacctaaatg catg                                                    74

<210> SEQ ID NO 13
<211> LENGTH: 6515
<212> TYPE: DNA
<213> ORGANISM: Artificial Sequence
<220> FEATURE:
<223> OTHER INFORMATION: Description of Artificial Sequence: primer

<400> SEQUENCE: 13
gcttgcatgc atttaggtga cactatagcg gccgcggatc cctatagtga gtcgtattac   60
ggaccgtaga gtcgagcagt gtggttttca agaggaagca aaaagcctct ccacccaggc  120
ctggaatgtt tccacccaat gtcgagcagt gtggttttgc agaggaagc aaaaagcctc  180
tccacccagg cctggaatgt tccacccaa tgtcgagcaa accccgccca gcgtcttgtc  240
attggcgaat tggaacacgc agatgcagtc ggggcggcg ggtcccaggt ccacttcgca  300
tattaaggtg acgcgtgtgg cctcgaacac cgagcgaccc tgcagcgacc cgcttaacag  360
cgtcaacagc gtgccgcaca tcttggtggc gtgaaactcc cgcacctctt cggccagcgc  420
cttgtagaag cgcgtatggc ttcgtacccc ggccatcagc acgcgtctgc gttcgaccag  480
gctgcgcgtt ctcgcggcca tagcaaccga cgtacgcgt tgcgccctcg ccggcagcaa  540
gaagccacgg aagtccgccc ggagcagaaa atgcccacgc tactgcgggt ttatatagac  600
ggtccccacg ggatggggaa aaccaccacc acgcaactgc tggtggccct gggttcgcgc  660
gacgatatcg tctacgtacc cgagccgatg acttactggc gggtgctggg ggcttccgag  720
acaatcgcga acatctacac cacacaacac cgccttgacc agggtgagat atcggccggg  780
gacgcggcgg tggtaatgac aagcgcccag ataacaatgg gcatgcctta tgccgtgacc  840
gacgccgttc tggctcctca tatcgggggg gaggctggga gctcacatgc cccgcccccg  900
gccctcaccc tcatcttcga ccgccatccc atcgccgcct tcctgtgcta cccggccgcg  960
cgataccta tgggcagcat gaccccccag gccgtgctgg cgttcgtggc cctcatcccg 1020
ccgaccttgc ccggcacaaa catcgtgttg ggggcccttc cggaggacag acacatcgac 1080
cgcctggcca aacgccagcg ccccggcgag cggcttgacc tggctatgct ggccgcgatt 1140
cgccgcgttt acgggctgct tgccaatacg gtgcggtatc tgcagggcgg cggtcgtgg 1200
cgggaggatt ggggacagct ttcggggacg gccgtgccgc ccagggtgc cgagcccag 1260
agcaacgcgg gccacgacc ccatatcggg gacacgttat ttaccctgtt tcgggccccc 1320
gagttgctgg cccccaacgg cgacctgtac aacgtgtttg cctgggcctt ggacgtcttg 1380
gccaaacgcc tccgtcccat gcacgtcttt atcctggatt acgaccaatc gccgccggc 1440
tgccgggacg ccctgctgca acttacctcc gggatgatcc agacccacgt caccaccca 1500

```
ggctccatac cgacgatctg cgacctggcg cgcacgtttg cacgggagat gggggaggct    1560
aactgaaaca cggaaggaga caataccgga aggaacctgc gctatgacgg caataaaaag    1620
acagaataaa acgcacgggt gttgggtcgt ttgttcataa acgcggggtt cggtcccagg    1680
gctggcactc tgtcgatacc ccaccgagac cccattgggg ccaatacgcc cgcgtttctt    1740
ccttttcccc accccacccc ccaagttcgg gtgaaggccc agggctcgca gccaacgtcg    1800
gggcggcagg cctgccatag ccacgggccc cgtgggttag ggacgggtcc cccatgggg    1860 aatggtttat ggttcgtggg ggttattatt ttgggcgttg cgtggggtca gtccacgact    1920
ggactgagca gacagaccca tggttttttgg atggcctggg catggaccgc atgtactggc    1980
gcgacacgaa caccgggcgt ctgtggctgc caaacacccc cgaccccaa aaaccaccgc    2040 gcggatttct ggcgccgccg gacgaactaa acctgactac ggaccgtcga cttaattaac    2100
atgccggcaa gtgcacaaac aatacttaaa taaatactac tcagtaataa cctatttctt    2160 agcattttg acgaaatttg ctattttgtt agagtctttt acaccatttg tctccacacc    2220
tccgcttaca tcaacaccaa taacgccatt taatctaagc gcatcaccaa catttctctgg   2280 cgtcagtcca ccagctaaca taaaatgtaa gctttcgggg ctctcttgcc ttccaaccca    2340
gtcagaaatc gagttccaat ccaaaagttc acctgtccca cctgcttctg aatcaaacaa    2400
gggaataaac gaatgaggtt tctgtgaagc tgcactgagt agtatgttgc agtcttttgg    2460
aaatacgagt cttttaataa ctggcaaacc gaggaactct tggtattctt gccacgactc    2520
atctccatgc agttggacga tatcaatgcc gtaatcattg accagagcca aaacatcctc    2580
cttaggttga ttacgaaaca cgccaaccaa gtatttcgga gtgcctgaac tattttttata   2640 tgctttttaca agacttgaaa ttttccttgc aataaccggg tcaattgttc tctttctatt    2700
gggcacacat ataatacccca gcaagtcagc atcggaatct agagcacatt ctgcggcctc    2760
tgtgctctgc aagccgcaaa ctttcaccaa tggaccagaa ctacctgtga aattaataac    2820
agacatactc caagctgcct ttgtgtgctt aatcacgtat actcacgtgc tcaatagtca    2880
ccaatgccct ccctcttggc cctctccttt tcttttttcg accgaattaa ttcgtaatca    2940
tggtcatagc tgtttcctgt gtgaaattgt tatccgctca caattccaca caacatacga    3000
gccggaagca taaagtgtaa agcctggggt gcctaatgag tgaggtaact cacattaatt    3060
gcgttgcgct cactgcccgc tttccagtcg ggaaacctgt cgtgccagct ggattaatga    3120
atcggccaac gcgcggggag aggcggtttg cgtattgggc gctcttccgc ttcctcgctc    3180
actgactcgc tgcgctcggt cgttcggctg cggcgagcgg tatcagctca ctcaaaggcg    3240
gtaatacggt tatccacaga atcaggggat aacgcaggaa agaacatgtg agcaaaaggc    3300
cagcaaaagg ccaggaaccg taaaaaggcc gcgttgctgg cgttttttcca taggctccgc    3360 ccccctgacg agcatcacaa aaatcgacgc tcaagtcaga ggtggcgaaa cccgacagga    3420
ctataaagat accaggcgtt tcccctggaa agctccctcg tgcgctctcc tgttccgacc    3480
ctgccgctta ccggatacct gtccgccttt ctcccttcgg gaagcgtggc gctttctcat    3540
agctcacgct gtaggtatct cagttcggtg taggtcgttc gctccaagct gggctgtgtg    3600
cacgaacccc ccgttcagcc cgaccgctgc gccttatccg gtaactatcg tcttgagtcc    3660
aacccggtaa gacacgactt atcgccactg gcagcagcca ctggtaacag gattagcaga    3720
gcgaggtatg taggcggtgc tacagagttc ttgaagtggt ggcctaacta cggctacact    3780
agaaggacag tatttggtat ctgcgctctg ctgaagccag ttaccttcgg aaaaagagtt    3840
```

```
ggtagctctt gatccggcaa acaaaccacc gctggtagcg gtggttttt tgtttgcaag    3900
cagcagatta cgcgcagaaa aaaggatct caagaagatc ctttgatctt ttctacgggg    3960
tctgacgctc agtggaacga aaactcacgt taagggattt tggtcatgag attatcaaaa   4020
aggatcttca cctagatcct tttaaattaa aaatgaagtt ttaaatcaat ctaaagtata   4080
tatgagtaaa cttggtctga cagttaccaa tgcttaatca gtgaggcacc tatctcagcg   4140
atctgtctat ttcgttcatc catagttgcc tgactccccg tcgtgtagat aactacgata   4200
cgggagggct taccatctgg ccccagtgct gcaatgatac cgcgagaccc acgctcaccg   4260
gctccagatt tatcagcaat aaaccagcca gccggaaggg ccgagcgcag aagtggtcct   4320
gcaactttat ccgcctccat ccagtctatt aattgttgcc gggaagctag agtaagtagt   4380
tcgccagtta atagtttgcg caacgttgtt gccattgcta caggcatcgt ggtgtcacgc   4440
tcgtcgtttg gtatggcttc attcagctcc ggttcccaac gatcaaggcg agttacatga   4500
tcccccatgt tgtgcaaaaa agcggttagc tccttcggtc ctccgatcgt tgtcagaagt   4560
aagttggccg cagtgttatc actcatggtt atggcagcac tgcataattc tcttactgtc   4620
atgccatccg taagatgctt ttctgtgact ggtgagtact caaccaagtc attctgagaa   4680
tagtgtatgc ggcgaccgag ttgctcttgc ccggcgtcaa tacgggataa taccgcgcca   4740
catagcagaa ctttaaaagt gctcatcatt ggaaaacgtt cttcggggcg aaaactctca   4800
aggatcttac cgctgttgag atccagttcg atgtaaccca ctcgtgcacc caactgatct   4860
tcagcatctt ttactttcac cagcgtttct gggtgagcaa aaacaggaag gcaaaatgcc   4920
gcaaaaaagg aataagggc gacacggaaa tgttgaatac tcatactctt ccttttcaa    4980
tattattgaa gcatttatca gggttattgt ctcatgagcg gatacatatt tgaatgtatt   5040
tagaaaaata acaaataggg gttccgcgc acatttcccc gaaaagtgcc acctgacgtc   5100
taagaaacca ttattatcat gacattaacc tataaaaata ggcgtatcac gaggccctt    5160
cgtctcgcgc gtttcggtga tgacggtgaa aacctctgac acatgcagct cccggagacg   5220
gtcacagctt gtctgtaagc ggatgccggg agcagacaag cccgtcaggg cgcgtcagcg   5280
ggtgttggcg ggtgtcgggg ctggcttaac tatgcggcat cagagcagat tgtactgaga   5340
gtgcaccata acgcatttaa gcataaacac gcactatgcc gttcttctca gtatatata    5400
tatacaggca acacgcagat ataggtgcga cgtgaacagt gagctgtatg tgcgcagctc   5460
gcgttgcatt tcggaagcg ctcgttttcg gaaacgcttt gaagttccta ttccgaagtt    5520
cctattctct agctagaaag tataggaact tcagagcgct tttgaaaacc aaaagcgctc   5580
tgaagacgca ctttcaaaaa accaaaaacg caccggactg taacgagcta ctaaaatatt   5640
gcgaataccg cttccacaaa cattgctcaa aagtatctct ttgctatata tctctgtgct   5700
atatccctat ataacctacc catccaccatt tcgctccttg aacttgcatc taaactcgac   5760
ctctacattt tttatgttta tctctagtat tactctttag acaaaaaat tgtagtaaga    5820
actattcata gagtgaatcg aaaacaatac gaaaatgtaa acatttccta tacgtagtat   5880
atagagacaa aatagaagaa accgttcata attttctgac caatgaagaa tcatcaacgc   5940
tatcactttc tgttcacaaa gtatgcgcaa tccacatcgg tatagaatat aatcggggat   6000
gcctttatct tgaaaaaatg cacccgcagc ttcgctagta atcagtaaac gcgggaagtg   6060
gagtcaggct tttttatgg aagagaaaat agacaccaaa gtagccttct tctaaccta    6120
acggacctac agtgcaaaaa gttatcaaga gactgcatta tagagcgcac aaaggagaaa   6180
aaaagtaatc taagatgctt tgttagaaaa atagcgctct cgggatgcat ttttgtagaa   6240
```

```
caaaaaagaa gtatagattc tttgttggta aaatagcgct ctcgcgttgc atttctgttc    6300
tgtaaaaatg cagctcagat tctttgtttg aaaaattagc gctctcgcgt tgcatttttg    6360
ttttacaaaa atgaagcaca gattcttcgt tggtaaaata gcgctttcgc gttgcatttc    6420
tgttctgtaa aaatgcagct cagattcttt gtttgaaaaa ttagcgctct cgcgttgcat    6480
ttttgttcta caaatgaag cacagatgct tcgtt                                6515
```

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 14

```
ccggctgcat ggatctgca                                                 19
```

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 15

```
agtccacgga aacgaaagac a                                              21
```

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 16

```
cttgcatgca tttaggtgac a                                              21
```

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 17

```
gtaatacgac tcactatagg g                                              21
```

<210> SEQ ID NO 18
<211> LENGTH: 65
<212> TYPE: DNA
<213> ORGANISM: Artificial Sequence
<220> FEATURE:
<223> OTHER INFORMATION: Description of Artificial Sequence: primer

<400> SEQUENCE: 18

```
gtgggtggac gggcgctcca ctccagggag caggcgacct gcacccaagg cagtctggag    60
catgc                                                                65
```

<210> SEQ ID NO 19
<211> LENGTH: 70
<212> TYPE: DNA
<213> ORGANISM: Artificial Sequence
<220> FEATURE:

-continued

```
<223> OTHER INFORMATION: Description of Artificial Sequence: primer

<400> SEQUENCE: 19
caagtagcgg tcaatggcca tagcagtcag gatgtaggtg ctggtgtgag tttagtatac      60
atgcatttac                                                             70
```

US 6,503,712 B1

METHODS AND COMPOSITIONS FOR PREPARING A GENOMIC LIBRARY FOR KNOCKOUT TARGETING VECTORS

FIELD OF THE INVENTION

The present invention relates to generation of genomic libraries in shuttle vectors and high throughput generation of vectors by homologous recombination for creating transgenic animals by homologous recombination.

BACKGROUND OF THE INVENTION

A particularly productive approach to understanding the function of a particular gene in animals involves the disruption of the gene's function by "targeted mutagenesis". A common form of targeted mutagenesis is to generate "gene knockouts". Typically, a gene knockout involves disrupting a gene in the germline of an animal at an early embryonic stage. (See, Thomas et al., Cell, 51:503 (1987).) Once established in the germline, it is possible to determine the effect of the mutation on the animal in both the heterozygous and homozygous states by appropriate breeding of mice having the germline mutation.

The mouse knockout model system is very useful for functional genomic analysis of genes. The advantages of mouse models for the study of mammalian physiology, and testing of therapies for the treatment of human diseases, and developmental abnormalities have been extensively established.

Among the many examples of the use of knockout technology utilized to investigate gene function are U.S. Pat. Nos. 5,625,122 and 5,530,178 to Mak, T. which describe the production of mice having a disrupted gene encoding lymphocyte-specific tyrosine kinase $p56^{lck}$ and Lyt-2, respectively. Silva et al., Science, 257:201 (1992) produced mice having a disrupted α-Calcium Calmodulin kinase II gene (αCaMKII gene) which resulted in animals having an abnormal fear response and aggressive behavior. (See, also, Chen et al., Science, 266:291 [1994]). Wang et al., Science, 269:1108 (1995) demonstrated that the disruption in mice of the C/EPBα gene which encodes a basic leucine zipper transcription factor results in impaired energy homeostasis in the mutant animals. Knudsen et al., Science, 270:960 (1995) demonstrated that disruption of the BAX gene in mice results in lymphoid hyperplasia and male germ cell death.

The most common approach to producing knockout animals involves the disruption of a target gene by inserting into the target gene (usually in embryonic stem cells), via homologous recombination, a DNA construct encoding a selectable marker gene flanked by DNA sequences homologous to part of the target gene. When properly designed, the DNA construct effectively integrates into and disrupts the targeted gene thereby preventing expression of an active gene product encoded by that gene.

Homologous recombination involves recombination between two genetic elements (either extrachromosomally, intrachromosomally, or between an extrachromosomal element and a chromosomal locus) via homologous DNA sequences, which results in the physical exchange of DNA between the genetic elements. Homologous recombination is not limited to mammalian cells but also occurs in bacterial cells, yeast cells, in the slime mold Dictyostelium discoideum and in other organisms. For a review of homologous recombination in mammalian cells, see Bollag et al., Ann. Rev. Genet., 23:199–225 (1989) (incorporated herein by reference). For a review of homologous recombination in fungal cells, see Orr-Weaver et al., Microbiol. Reviews, 49:33–58 (1985) incorporated herein by reference.

With the increasing awareness that animal, and particularly mouse mutations can provide such useful insights about the function of genes from humans, a great deal of interest is developing to systematically generate mutations within genes in mice that correspond to those genes which are being isolated and characterized as part of various genome initiatives such as the Human Genome Project. The problem with utilizing these procedures for large-scale mutagenesis experiments is that the technologies for generating transgenic animals and targeted mutations are currently very tedious, expensive, and labor intensive. The most tedious parts of making an animal knockout construct from a given cDNA is obtaining an appropriate genomic fragment and gene mapping. Once the genomic fragment is obtained and mapped, actual assembly of the targeting vector also is a tedious process depending upon availability of appropriate restriction sites.

Generally, the preparation of these constructs requires isolating genomic clones containing the region of interest, developing restriction maps, engineering restriction sites into the clones, and restriction digesting and ligating fragments to engineer the specific construct needed to produce the knockout. See, e.g., Mak, T. U.S. Pat. Nos. 5,625,122 and 5,530,178; Joyner et al., Nature, 338:153–156 (1989); Thomas et al., supra; Silva et al., supra, Chen et al., supra; Wang et al., supra; and Knudsen et al., supra. This is a long and tedious process that can take several months to complete. Thus, in order to more rapidly and efficiently create model organisms with genomic modifications, there exists a need to develop high throughput methods for the production of targeting constructs which do not require identification of target genomic fragments by traditional means, their cloning, and subsequent restriction mapping and other complex molecular engineering steps.

SUMMARY OF THE INVENTION

The present invention, in preferred embodiments, provides methods of preparing a genomic library for use in producing knockout targeting vectors comprising preparing a size selected mouse genomic DNA; preparing a shuttle vector comprising inserting said genomic DNA into a yeast vector, wherein the vector comprises a first bacterial origin of replication; a first bacterial selection marker; a first yeast origin of replication; a first yeast selection marker; and a first mammalian selection marker; transforming bacterial host cells with said shuttle vector to amplify said genomic library; arraying said transformed host cells into pools of cloned cells comprising shuttle vectors comprising a genomic DNA fragment; a first yeast origin of replication; a first yeast selection marker; a first bacterial origin of replication; a first bacterial selection marker; and a first selection marker for integration into mammalian cells; wherein the cells in said pools comprise mouse genomic fragments of different size.

In specific embodiments, the genomic DNA is a library which comprises mouse genomic DNA fragments ranging from about 8 kb to about 14 kb.

More particularly, the mouse genomic DNA fragments are isolated from a mouse strain selected from the group consisting of 129svj, 129 Ola, 129sv, and C57BL/6. Of course, these are merely exemplary strains of mice and those of skill in the art will be aware that other mouse strains may be employed for generating the transgenic animals of the present invention. Likewise, while certain preferred embodiments are directed to the generation of transgenic mice, it should be understood that the present invention is equally applicable to generating transgenic animals of other species such as, for example, mammals including but not limited to rabbits, mice, rats, hamsters, goats, sheep, pigs, horses, cows, dogs, cats, as well as primates, such as, monkeys, apes, and baboons.

In specific embodiments, the genomic library, when transformed into the bacterial host cells with said shuttle vector generates between about $3 \times 10^6$ and $5 \times 10^6$ clones. This is an exemplary range and it is contemplated that those of skill in the art may prepare a genomic library that generates more or fewer clones. Thus the practice of the invention may generate about $1 \times 10^6$ clones, about $2 \times 10^6$ clones, about $3 \times 10^6$ clones, about $4 \times 10^6$ clones, about $5 \times 10^6$ clones, about $6 \times 10^6$ clones, about $7 \times 10^6$ clones, about $8 \times 10^6$ clones, about $9 \times 10^6$ clones, about $10 \times 10^6$ clones or more clones or indeed may generate less than $1 \times 10^6$ clones and still provide meaningful shuttle vectors that may be used in the context of the present invention. The host cells that are available for transformation can be any host cell well known to those of skill in the art. In preferred embodiments, the host cells are bacterial cells selected from the group consisting of *Escherichia coli, Bacillus subtilis, Pseudomonas aeruginosa, Salmonella typhimurium* and *Serratia marcescans*. Particularly preferred host cells are *E. coli*.

In preferred embodiments, the shuttle vector comprises a bacterial origin of replication selected from the group consisting of ColE1-ORI, F and R1. Preferably, the bacterial origin of replication is an *E. coli* origin of replication. In specific embodiments, the *E. coli* origin of replication is ColE1-ORI. The yeast origin of replication preferred in the context of the preferred vectors of the present invention is selected from the group consisting of Cen, $2\mu$ and the autonomous replication sequence.

The shuttle vectors may employ any selectable marker commonly used to monitor bacterial propagation, yeast propagation and selection in mammalian cells. In preferred embodiments, the marker for bacterial propagation is selected from the group consisting of ampicillin resistance, tetracycline resistance, neomycin resistance, kanamycin resistance and chloramphenicol resistance. These are merely exemplary and additional markers will be well known to those of skill in the art and are contemplated to be useful in the present invention. In preferred embodiments, the bacterial propagation marker for ampicillin resistance is BlaI.

Those of skill in the art will understand that any yeast selectable marker may be advantageously employed in the shuttle vectors of the present invention. In preferred embodiments, the marker for propagation in yeast is selected from the group consisting of trp1, His, Ura3, Arg, Ade and Leu2. The selectable marker for mammalian cells may be selected from the group consisting of neomycin resistance, hygromycin resistance, zeocin resistance, Salmonella HisD and puromycin N-acetyl transferase. In certain embodiments, the vectors may further comprise a negative selectable marker. In specific embodiments, the negative selectable marker is selected from the group consisting of thymidine kinase, and xanthine-guanine-phosphoribosyltransferase.

In particularly preferred embodiments, the yeast vector of the present invention comprises a BamHI site for inserting said genomic fragments. More particular embodiments contemplate that the BamHI site is flanked by priming sequences to facilitate PCR amplification. Generally, priming sequences for PCR amplification are well known to those of skill in the art; preferably, the priming sequences arc Sp6 and T7 priming sequences. In particularly preferred embodiments, the yeast vector of the present invention is the vector designated as pYYL-1.

In specific aspects the shuttle vector further comprises rare cutting enzyme sites flanking the genomic fragment. More specifically, the shuttle vector comprises rare cutting enzyme sites flanking the mammalian selection marker. In preferred aspects of the present invention, the mouse genomic library described by the present invention is used for high throughput construction of knockout vectors, and more specifically mouse knockout vectors.

Another aspect of the present invention contemplates a method for the preparation of a gene targeting vector for homologous recombination comprising selecting a bacterial clone pool positive for the gene to be targeted from an array of bacterial clones comprising the mouse genomic library described above; isolating the DNA from said positive pool; preparing a second expression construct comprising a marker cassette comprising a second yeast selectable marker and a second mammalian selectable marker, wherein said marker cassette is flanked on each side by mammalian gene-specific sequences homologous for a portion of the gene to be targeted; transforming yeast cells with the second expression construct and the DNA from the positive clone; selecting the transformed yeast cells for expression of the first and second yeast selectable markers; and isolating the targeting vector produced by the recombination between the shuttle vector and the second expression construct.

In specific embodiments, the positive pools comprising the target gene are selected by PCR analysis of the pools with gene-specific PCR primers wherein amplification of the PCR products is indicative of the pool comprising the target gene of interest. PCR amplification techniques are well known to those of skill in the art and are described in for example Sambrook et al., Molecular Cloning: A Laboratory Manual, Cold Spring Harbor Laboratory Press, Cold Spring Harbor, N.Y., (1989).

In preferred embodiments, the gene-specific flanking sequences each comprises at least about 20 nucleotides. In other embodiments, the gene specific flanking sequences each comprises from about 35 to about 400 nucleotides. This is an exemplary range and it is contemplated that the gene specific flanking sequences may comprise for example, about 20, about 25, about 30, about 35, about 40, about 45, about 50, about 55, about 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, about 450, about 500, about 550, about 600, about 650, about 700, about 750, about 800, about 850, about 900, about 950, about 1000 or more nucleotides.

In specific embodiments, the fragment of genomic DNA comprises from about 0.5 kb to about 5 kb of DNA on each side of a site in said gene to be targeted. This is merely an exemplary range and it is contemplated that the fragment of genomic DNA may comprise about 0.5 kb, 0.6 kb, 0.7 kb, 0.8 kb, 0.9 kb, 1.0 kb, 1.2 kb, 1.4 kb, 1.5 kb, 1.6 kb, 1.7 kb, 1.8 kb, 1.9 kb, 2.0 kb, 2.25 kb, 2.5 kb, 2.75 kb, 3.0 kb, 3.25 kb, 3.5 kb, 3.75 kb, 4.0 kb, 4.25 kb, 4.5 kb, 4.75 kb, 5.0 kb, 5.5 kb, 6.0 kb, 6.5 kb, 7.0 kb or more of DNA on each side of a site in said gene to be targeted. In particularly preferred embodiments, the fragment of genomic DNA comprises at least about 1 kb of genomic DNA on each side of a site in said gene to be targeted. In certain embodiments, the second yeast selectable marker is selected from the group consisting of TRP1, His, Ura3, Ade, Arg and Leu2. In other embodiments, the second mammalian selectable marker is selected from the group consisting of consisting of thymidine kinase, neomycin resistance, hygromycin resistance, Salmonella HisD and puromycin N-acetyl transferase. In specific embodiments, it is contemplated that the marker cassette comprises Ura3 as the second yeast selectable marker and the neomycin resistance gene as the second mammalian selectable marker.

BRIEF DESCRIPTION OF THE DRAWINGS

The following drawings form part of this application and are included to further demonstrate certain aspects of the invention. The invention may be better understood by reference to one or more of these drawings in combination with the detailed description of the specific embodiments of the present invention.

FIG. 3 shows a flow diagram describing generation of a recombined knockout cassette according to the present invention.

DETAILED DESCRIPTION OF THE PREFERRED EMBODIMENTS

Figure 1:
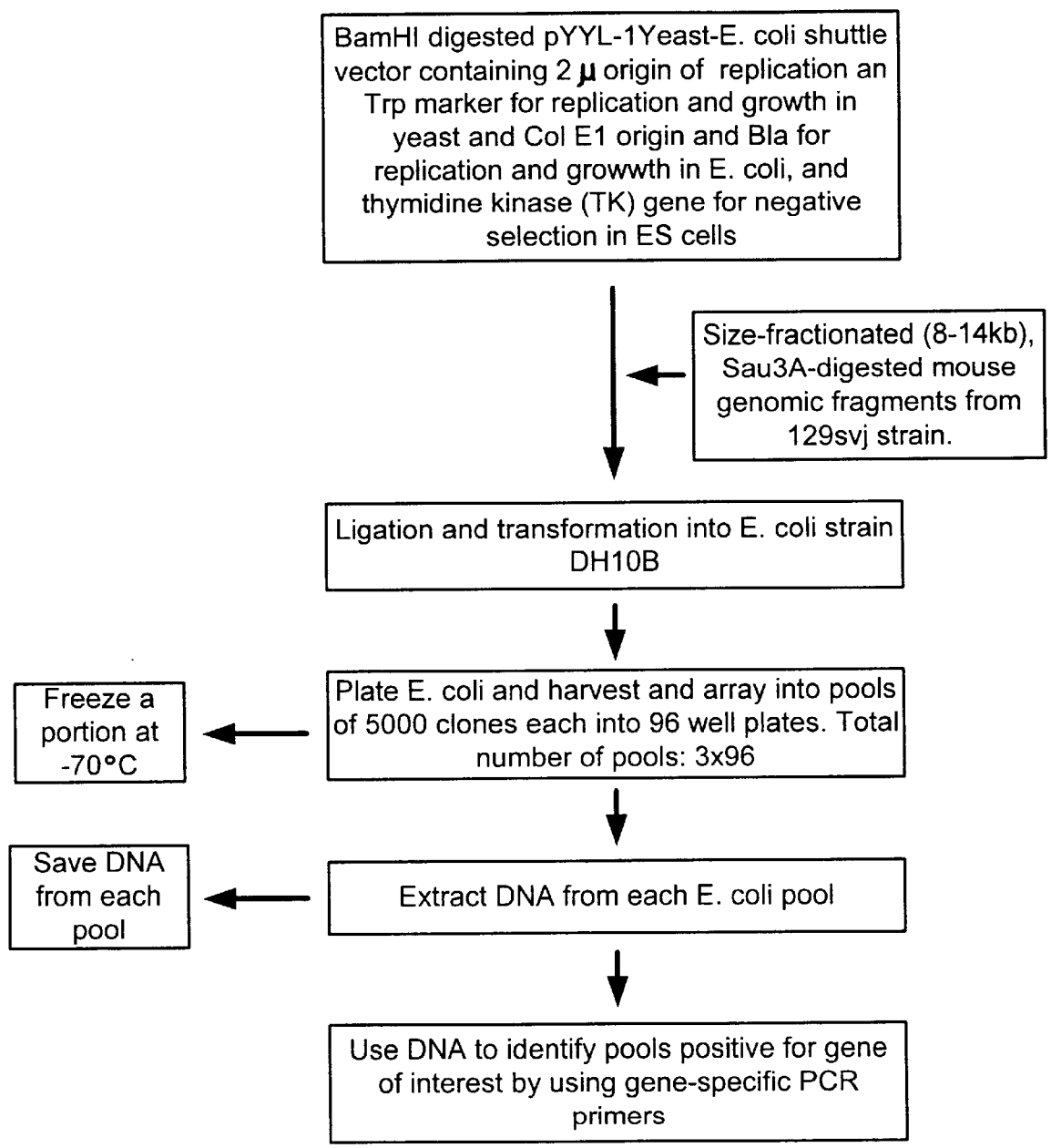
FIG. 1 shows a flow diagram describing the construction and arraying of mouse genomic library into a yeast-E. coli shuttle vector.

Traditional methods of generating knockout animals involve the isolation of a specific genomic sequence from a given animal for example, a mouse which is then employed in the specific targeting construct to generate the appropriate knockout vector. In such conventional method, cDNA is used to obtain a corresponding genomic bacterial artificial chromosome (BAC) clone/s, followed by extensive mapping and Southerns for selection of appropriate-sized fragments. These fragments must then be sub-cloned into an appropriate vector for construction of knockout cassette. Appropriate restriction enzyme sites must be present in order to remove the targeted area within the coding region and to replace it with a mammalian selection marker. In addition, this process of identifying BACs, subcloning and making conventional knockout cassette must be repeated for each knockout desired. This traditional technique is laborious and time consuming.

The present invention reduces the number of cloning steps required for creating a mouse knock-out targeting vector to a single insertion of a selection cassette by using a mouse genomic library and a recombination cassette. Prior knowledge of genomic structure of the gene of interest is not required, which is another major advantage of the system.

More particularly, in the present invention, homologous recombination in yeast in a high throughput setting is employed to construct a mouse genomic library in yeast-E. coli shuttle vector(s). Construction of the mouse knock-out targeting vector is then achieved in a single homologous recombination step using the mouse genomic library in the yeast vector. This method is advantageous in that it provides a readily available library for the generation of knockout constructs, thereby saving time and cost.

The method described herein allows the generation of knockout targeting vectors within two to three weeks beginning with the screening of the arrayed genomic library in the E. coli-yeast shuttle vector. In preferred aspects the arrayed genomic library is generated from a mouse, however, as stated above the techniques described herein will be useful for the production of other transgenic animals. Vectors generated by this method allow both positive and negative selection.

Positive selection is applied to select for cells that stably integrate the positive selection marker of the targeting vector. Negative selection is applied to select against those cells in which either an integration or a non-homologous recombination event causes incorporation of the negative selection cassette. Methods and compositions for preparing the library, targeting constructs and transgenic animals are described in further detail.

I. Homologous Recombination Using Arrayed Genomic Libraries

The present invention is directed to providing more efficient methods of creating vectors using homologous recombination. More particularly the present invention discloses methods of making and using mouse genomic libraries arrayed in shuttle vectors to create targeting vectors for producing knock-out mice.

Homologous recombination relies on the tendency of nucleic acids to base pair with complementary sequences. In this instance, the base pairing serves to facilitate the interaction of two separate nucleic acid molecules so that strand breakage and repair can take place. in other words, the "homologous" aspect of the method relies on sequence homology to bring two complementary sequences into close proximity, while the "recombination" aspect provides for one complementary sequence to replace the other by virtue of the breaking of certain bonds and the formation of others.

Put into practice, homologous recombination in the context of the present invention is used as follows. First, a target gene is selected within the host cell. Sequences homologous to the target gene are then included in a genetic construct, along with some mutation that will modify the activity of the target gene (stop codon, interruption, deletion, constitutive mutation, etc.). The homologous sequences on either side of the modifying mutation are said to "flank" the mutation. Flanking, in this context, simply means that target homologous sequences are located both upstream (5') and downstream (3') of the mutation. These sequences should correspond to some sequences upstream and downstream of the target gene. The construct is then introduced into the cell, thus permitting recombination between the cellular sequences and the construct.

Targeted mutagenesis of a gene will result in an alteration (e.g., partial or complete inactivation or constitutivity) of normal production or structure of the polypeptide encoded by the targeted gene of a single cell, selected cells or all of the cells of an animal (or in culture) by introducing an appropriate targeting construct into a site in the gene to be disrupted.

Targeted mutagenesis may also refer to "knocking in" a gene which means replacing one gene with all or part of another gene from the same or a heterologous organism for the purpose of determining, for example, whether two genes are functionally equivalent (see, e.g., Hanks et al., *Science*, 269:679 (1995), incorporated herein by reference), although other applications are possible. For example, transcriptional regulatory sequences such as promoters may be knocked in to a region of a genome so as to be operatively linked to a structural sequence.

As a practical matter, the genetic construct will normally act as far more than a vehicle to interrupt the gene. For example, it is important to be able to select for recombinants and, therefore, it is common to include within the construct a selectable marker gene. This gene permits selection of cells that have integrated the construct into their genomic DNA by conferring resistance to various biostatic and biocidal drugs. In addition, a heterologous gene that is to be expressed in the cell also may advantageously be included within the construct. The arrangement may be as follows:

... vector ... 5'-flanking sequence ... heterologous gene ... selectable marker gene ... flanking sequence-3' . . . vector ...

Thus, using this kind of construct, it is possible, in a single recombinatorial event, to (i) "knock out" an endogenous gene, (ii) provide a selectable marker for identifying such an event and (iii) introduce a heterologous gene for expression.

In most cases, targeting constructs are constructed so as to include at least a portion of a gene to be disrupted. Typically, the portion of the gene included in the targeting construct is interrupted by insertion of a marker sequence (usually a selectable marker) that disrupts the reading frame of the interrupted gene so as to preclude expression of an active gene product. This most often causes a knock out or inactivation of a gene.

Another refinement of the homologous recombination approach involves the use of a "negative" selectable marker. This marker, unlike the selectable marker, causes death of cells which express the marker. Thus, it is used to identify undesirable recombination events. When seeking to select homologous recombinants using a selectable marker, it is difficult in the initial screening step to identify proper homologous recombinants from recombinants generated from random, non-sequence specific events. These recombinants also may contain the selectable marker gene and may express the heterologous protein of interest, but will, in all likelihood, not have the desired "knock out" phenotype. By attaching a negative selectable marker to the construct, but outside of the flanking regions, one can select against many random recombination events that will incorporate the negative selectable marker. Homologous recombination will likely not introduce the negative selectable marker, as it is outside of the flanking sequences.

Thus, for preparing knockouts, a gene within a host cell is chosen as the target gene into which a selection marker gene is to be transferred. Sequences homologous to the target gene are included in the expression vector, and the selection gene is inserted into the vector such that target gene homologous sequences are interrupted by the selection gene or, put another way, the target gene homologous sequences "flank" the selection gene. In preferred embodiments, a drug selectable marker gene also is inserted into the target gene homologous sequences. Given this possibility, it should be apparent that the term "flank" is used broadly herein, namely, as describing target homologous sequences that are both upstream (5') and downstream (3') of the heterologous gene and/or the drug selectable marker gene. In effect, the flanking sequences need not directly abut the genes they "flank." Application of a drug to such cells will permit isolation of recombinants, in that expression of the marker in the cells will confer drug resistance whereas cells that do not express that targeting sequence will not be resistant to the drug and will die when grown in the presence of the drug.

Similarly, targeting constructs designed for knocking in genes can recombine at the homologous genomic site by homologous recombination and will result in the introduction of all or a portion of a gene into that locus. Techniques for knocking in genes are described in detail in Hanks et al., *Science*, 269:679 (1995) which is incorporated herein by reference. Methods for homologous recombination specific to the present invention and methods of introducing the knockout mutation into the germline of an animal are described in further detail below.

Practice of the invention involves preparing genomic library from a selected mouse strain in yeast-*E. coli* shuttle vector and a recombination cassette for producing the targeting vector by homologous recombination. The invention preferably involves preparing at least two DNA constructs, a yeast shuttle vector comprising the genomic DNA from a selected mouse strain and a recombinant cassette for producing the homologous recombination.

The yeast shuttle vector comprising the library of DNA fragments isolated from the mouse strain generally comprises a yeast selectable marker, a bacterial selectable marker and a mouse genomic DNA fragment. The mouse genomic DNA is size fractionated into fragments of between about 8 kb to about 14 kb of the total mouse genomic DNA. As such, the fragments may contain all or a portion of any number of genes.

The recombination cassette of the present invention generally will comprise unique flanking sequences which are different from one another and which correspond to sequences in the genomic site that is to be targeted. Interposed between the flanking sequences may be positioned a sequence that encodes a marker. This sequence will thus have a two fold function in that it will act as a marker for the homologous recombination as well as acting as a disruption sequence. Alternatively, a transcriptional regulatory sequence or a combination of a marker sequence disposed 5' to a transcriptional regulatory sequence may be interposed between the flanking sequences.

The genomic library in the yeast shuttle vector and the recombination cassette are introduced into yeast cells which mediate recombination between the homologous sequences in the shuttle vector and the recombination cassette, effectively introducing the DNA interposed between the unique flanking DNA into the fragment of genomic DNA in the shuttle vector. The resulting targeting construct may be used, as described above, to produce targeted mutations.

It should be noted that the DNA sequences involved in homologous recombination according to any aspect of the present invention need not be 100% homologous with one another (or identical), however in general, the greater the homology between sequences the greater the efficiency of recombination.

In preferred aspects of the present invention, to generate the recombination cassette for any gene of interest, two (i.e., a sense and antisense) oligonucleotide primers are synthesized of which 45 nucleotides are homologous to the targeted area of the gene of interest. In addition to the homology to the target region, the sense primer at its 3' end also contains additional 20 bp that correspond to 5' end of the neomycin gene. In the antisense primer, 20 bp at the 3' end are homologous to the 3' end of the URA3 gene. Using these primers, a 2.8 kb cassette is generated that has 45 bp flanking sequences at its ends that are homologous to the gene of interest. This homology is used for directed recombination of the cassette with the gene of interest within the mouse genomic library in yeast.

The yeast *Saccharomyces cerevisiae* has highly developed genetic systems involving homologous recombination that have been very useful for genetic engineering in vivo (see, e.g., Orr-Weaver et al., *Microbiol. Rev.*, 49:33 [1985]). In yeast, linear double-stranded (ds) DNA undergoes efficient homologous recombination with either chromosomal or plasmid targets (Orr-Weaver et al., supra). The present invention is directed to exploiting the yeast homologous recombination system in order to increase the efficiency of production of targeting constructs for the generation of targeted mutations (e.g., knock out or knock in mutations). Specifically, yeast-*E. coli* shuttle vectors are generated in which the whole mouse genomic DNA in fragments of between about 8 kb to about 14 kb is arrayed in pools of *E. coli* clones.

According to the present invention, homologous recombination in yeast allows the preparation of targeting constructs to target essentially any segment of the mouse or other mammalian genome. Unlike the traditional methods used to make targeting constructs, the methods of the present invention do not require detailed restriction mapping, convenient restriction sites, or the engineering of restriction sites, but instead use a genomic clone comprising a fragment containing at least a part of an exon of a target gene or a portion of the locus to be targeted (including 5 or 3' untranslated sequences or intron sequences). Using polymerase chain reaction (PCR) primers to determine whether a particular clone comprises such a targeted gene will allow one of skill in the art to produce knock-out targeting vectors with limited sequence information regarding the exon or locus of the target gene. The approach is exemplified below with reference to particular genes and particular mouse strains, however, the methods of the present invention are readily adaptable to other genes and other species of mice and other mammals. The general method of the invention is depicted schematically in FIGS. 1 through 3 in which FIG. 1 describes the construction and arraying of the mouse genomic library in pools of clones and FIGS. 2 and 3 describe the use of the genomic library to create knock out vectors for homologous recombination.

Figure 2:
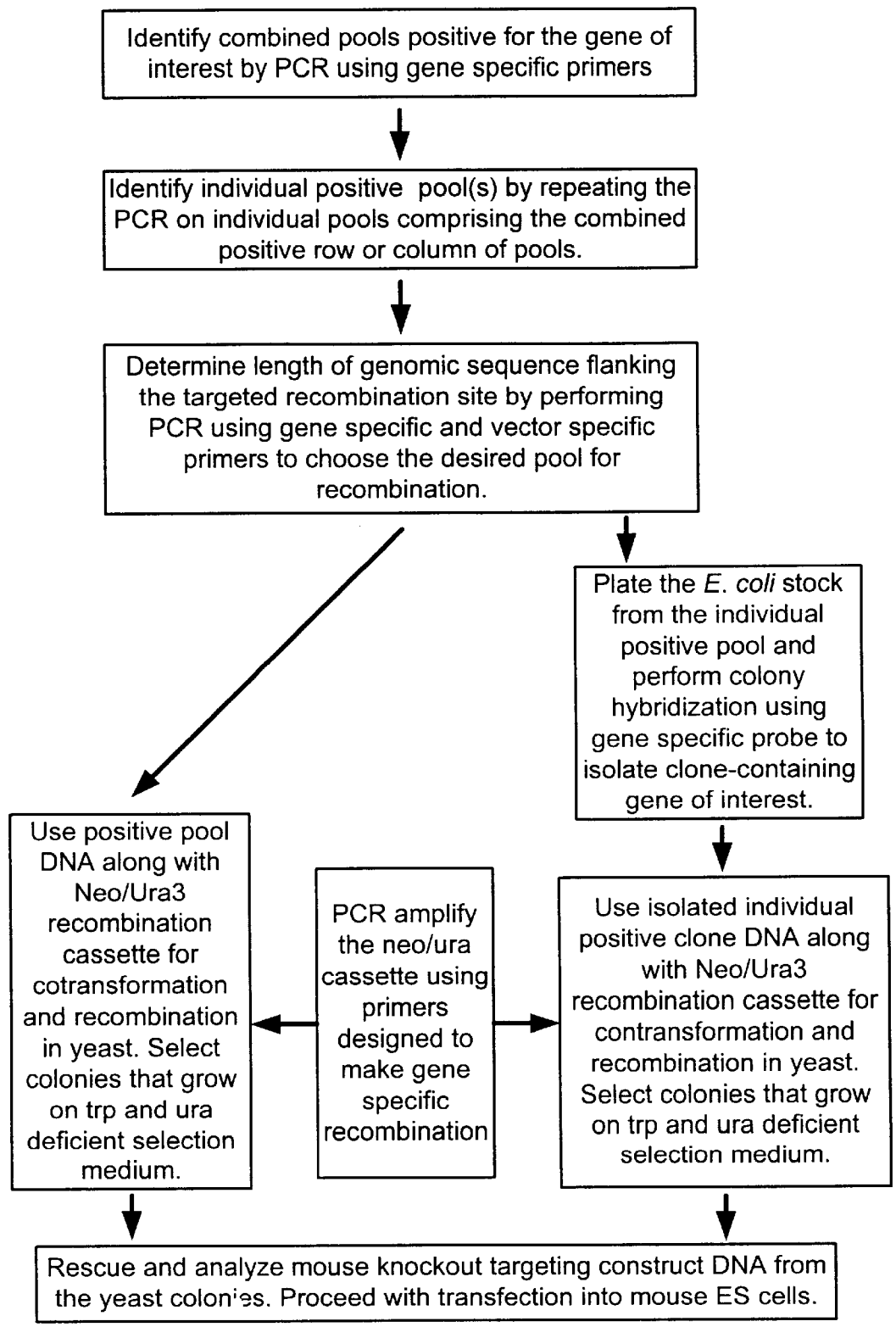
FIG. 2 shows a flow diagram describing the construction of knock-out vectors from pooled mouse genomic library by using yeast homologous recombination.

By way of overview and with reference to FIGS. 1 through 3, a library of fragments of mouse 129/Svj (see, e.g., Knudsen et al., *Science*, 270:96 (1995)) genomic DNA obtained from a genomic library of 129/sv DNA containing at least part of the gene to be targeted is cloned into a yeast/*E. coli* shuttle vector which has selectable markers allowing selection in yeast, *E. coli* and in mammalian cells. A selection or marker gene generally encodes a polypeptide, which allows for maintenance of the plasmid in a population of cells. Some selection markers can also be used negatively in which loss of the marker confers viability to the host cells under certain growth conditions. Typical proteins include those that confer resistance to antibiotics or other toxins or allow growth in the presence of specific nutrients.

Markers for selection in yeast are well known to those of skill in the art and include those involved in growth on specific sugar and amino acid substrates, such as trp, ura, leu, ade and his genes, which provide for maintenance of the plasmid in transformed yeast host cells lacking the corresponding functional genes on the host chromosome. Markers for selection in bacterial cells such as *E. coli* include those conferring resistance to antibiotics such as ampicillin, chloramphenicol, kanamycin, and the like. Positive and negative markers for selection of mammalian cells also will be used. Positive marker genes functional in mammalian cells include neomycin resistance, zeocin resistance, and hygromycin resistance markers, whereas negative selection markers may include TK (thymidine kinase) and XGPRT (xanthine-guanine-phosphoribosyltransferase).

Generally, negative selection markers may code for enzymes, which convert nucleotide analogs to products which are lethal upon incorporation into DNA. More particularly, TK is a versatile selection marker because cells can be selected for either loss or acquisition of this gene under different growth conditions. TK selection has proven useful for generation of cellular and viral gene knockouts. The presence of the thymidine kinase gene may be detected by the use of nucleoside analogs such as acyclovir or Gancyclovir which will induce cytotoxic effects on cells that contain a functional thymidine kinase gene. The absence of sensitivity to these nucleoside analogs indicates the absence of the thymidine kinase gene.

In an exemplary embodiment, genomic DNA from the liver of 129svj mouse strain is isolated using the procedure described in Molecular Cloning: A laboratory manual (Molecular Cloning: A Laboratory Manual, Cold Spring Harbor Laboratory Press, Cold Spring Harbor, N.Y., 1989). The mouse genomic DNA derived from other mouse strains such as 129 Ola, 129sv, C57BL/6 also may be used for the purpose of making mouse genomic library. The purified high-molecular-weight genomic DNA is partially digested with Sau3A restriction enzyme to randomly fragment the DNA and to obtain directly clonable ends. This DNA is then subjected to size fractionation through a sucrose density gradient. (Maniatis, T. et al. (1978). The isolation of structural genes from libraries of eukaryotic DNA. Cell 15: 687). Additional methods of size fractionation also are contemplated for the present invention. Such fractionation should yield fractions containing 8–14 kb genomic fragments which are subsequently cloned into the yeast-*E. coli* shuttle vector.

The shuttle vector into which the genomic DNA is cloned has to be capable of propagation in both yeast cells and in *E. coli*. In the yeast cells the shuttle vector will serve as a target for recombination and generation of the targeting vector and in the *E. coli* cells the shuttle vector will be amplified to obtain significant amounts of the shuttle vector. The shuttle vectors are prepared according to techniques well known to those of skill in the art, see for example, Sambrook et al., Molecular Cloning: A Laboratory Manual, Cold Spring Harbor Laboratory Press, Cold Spring Harbor, N.Y., (1989); by Ausubel et al., Eds. Current Protocols in Molecular Biology, Current Protocols Press, (1994); and by Berger and Kimmel, Methods in Enzymology: Guide to Molecular Cloning Techniques, Vol. 152, Academic Press, Inc., San Diego, Calif., (1987), the disclosures of which are hereby incorporated by reference.

In preferred aspects, the present invention employs yeast-*E. coli* shuttle vectors to generate the constructs for the production of knockout mice. Those of skill in the art will understand that the shuttle vector may be any yeast vector that is amenable for use in homologous recombination. As such, it is contemplated that shuttle vectors such as, pRS416 and pRS426 (Sikorski et al., *Genetics*, 122:19–27 (1989); Christian et al., *Gene*, 110:119–122, incorporated herein by reference) will be useful starting vectors for the construction of the shuttle vectors of the present invention.

In preparing the mouse genomic libraries, the vectors are first restriction digested to eliminate vector background. The digested vector is then dephosphorylated in order to decrease the likelihood of vector self ligation. The dephosphorylated vectors are then mixed with and ligated to the size fractionated, Sau3A digested mouse genomic fragments to produce a vector comprising the mouse genomic DNA.

The shuttle vectors of the invention require an origin of replication functional in yeast and also an origin of replication functional in bacteria. Yeast replication origins include Cen, 2μ and autonomous replication sequence (ARS). Preferably, the origin is a 2μ origin. Replication origins functional in bacteria are well known (e.g., ColE1, F, or R1 based origins) and may give low or high copy numbers. A preferred origin of replication functional in bacteria is a ColE1-type such as that present on plasmid pBR322. Where marker genes are employed in the vectors, depending on the nature of the marker gene, the marker may comprise transcriptional regulatory regions, particularly initiation regulatory regions.

Promoters and enhancers that will be useful regulatory regions in such a context are well known to those of skill in the art and include but are not limited to the HSV thymidine kinase (TK) promoter, human cytomegalovirus (CMV) immediate early gene promoter, the SV40 early promoter, the Rous sarcoma virus long terminal repeat promoter, β-actin promoter, rat insulin promoter, the phosphoglycerol kinase promoter and glyceraldehyde-3-phosphate dehydrogenase promoter, all of which are promoters well known and readily available to those of skill in the art, can be used to obtain high-level expression of the coding sequence of interest.

Inducible or regulatable promoters also are specifically contemplated, such as, for example, those that are hormone or cytokine regulatable. Hormone regulatable promoters include MMTV, MT-1, ecdysone and RuBisco as well as other hormone regulated promoters such as those responsive to thyroid, pituitary and adrenal hormones. By employing a promoter with well known properties, the level and pattern of expression of the protein of interest following transfection or transformation can be optimized. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization. Enhancers useful in the present invention are well known to those of skill in the art and will depend on the particular expression system being employed (Scharf D et al (1994) *Results Probl Cell Differ* 20: 125–62; Bittner et al (1987) *Methods in Enzymol* 153: 516–544).

In addition to the shuttle vector comprising the genomic library, a specific recombination cassette also is generated by using PCR. Such a cassette generally may contain markers for selection in yeast and in ES cells. In specific embodiments, the recombination cassette comprises the neomycin gene under the PGK promoter for ES selection and yeast nutritional marker URA3 gene provides for selection in yeast cells. The "Neo/Ura3" cassette-containing plasmid, pYYL-2 provides the universal template for creating knockout recombinant cassettes for any gene of interest by PCR amplification. After PCR, the neo/ura3 cassette is flanked on each side by about 40 base pairs of unique sequences corresponding to the region of the gene to be disrupted and through which homologous recombination will occur. The selection of DNA sequence for use as unique flanking sequences may be made based on the cDNA sequence of the gene or locus to be targeted or the genomic sequence but does not require the presence of known restriction sites nor does it require that restriction sites be engineered into the unique genomic DNA. It should be noted that the recombination cassette may also comprise a single marker sequence which allows selection in both yeast and ES cells. The length of the unique flanking sequences may vary from about 10 to 200 base pairs or more. Preferred lengths are from about 40 to about 200 base pairs although longer sequences may increase the efficiency of recombination. Lengths of 1 kb may be advantageous to the efficiency of homologous recombination.

Other exemplary selectable markers include genes conferring resistance to hygromycin, genes encoding the Salmonella his D gene (which allows a cell to convert histidinal to histidine), puromycin D-acetyl transferase and others. The markers used are not limited to those disclosed above but also include a variety of other selectable markers well known in the art and which are useful for selection in yeast, *E. coli*, and/or mammalian cells.

The DNA of the pool containing the shuttle vector, or the individual vector, comprising all or part of the genomic region to be targeted and the recombination cassette are introduced into a yeast strain by, for example, lithium acetate transformation or by electroporation (or by other methods known in the art) either sequentially or simultaneously.

Once in the yeast cell, the recombination cassette and the shuttle vector can recombine by homologous recombination via their homologous gene sequences (i.e., the flanking sequences of the recombination cassette and the genomic sequence in the shuttle vector), thereby inserting, into the target DNA sequence in the shuttle vector, the marker or markers from the recombination cassette thereby generating a targeting construct. The targeting construct sequences will contain integrated markers that can be used in the selection of the recombination cassette flanked by sequences of the targeted gene by applying selection for the yeast marker used.

In preferred embodiments, the yeast strain YLU-100 (Mata ura3-52 lys2-801 ade2-101 trp1-D63 his3-D200, leu2-D1 Dsec7l:: His3) was used to generate the mouse knock-out vector. In order to determine if homologous recombination has occurred, the yeast is grown on media that will allow for selection according to the markers employed in the shuttle vector and the recombination cassette. If serial transformation is used, first the yeast is transformed with the DNA of the genomic clone or the pool containing the desired genomic clone and selected on growth medium that will allow for selection of using the yeast marker in the shuttle vector, e.g., growth on trp-deficient growth medium where the shuttle vector marker is TRP1. Subsequent transformation with the target recombination cassette and its successful recombination with the target genomic fragment is selected on the trp-deficient and ura-deficient growth medium where the yeast marker in the recombinant cassette is URA3. Alternatively, if cotransformation of genomic clone or pool containing the genomic clone is performed along with the recombination cassette, the yeast containing the recombinant mouse knock-out targeting vector is selected on trp- and ura-deficient growth medium.

To confirm that the integration of the recombination cassette occurred by homologous recombination as opposed to some random integration, targeted plasmids may then analyzed by PCR using a primer from each side of the insertion. Finally, the targeting vector containing the insertion is shuttled into bacteria so that adequate quantities of purified construct (e.g., plasmid) DNA can be prepared for final analysis and introduction into ES cells. In this way, targeting vectors can be generated with considerable ease and speed, obviating the extensive gene mapping and the search for suitable restriction sites required by traditional methods. It should be noted that the ease of construction and selection of targeting vectors according to the methods of the present invention readily lends itself to automated procedures, particularly when certain physically detectable (e.g., colorimetric, fluorometric, and others) markers are used for selection of the targeting vector.

II. Mouse Genomic Library Preparation and Amplification

The shuttle vectors of the present invention comprise genomic DNA fragments generated from mice. The genomic DNA is isolated according to methods well known to those of skill in the art and may be derived from any animal that is to be used to create a transgenic model. (Sambrook et al., 1989 Molecular Cloning: A laboratory manual, second edition). In preferred embodiments, the genomic DNA is derived from the 129svj mouse strain. Mouse genomic DNA derived from other mouse strains such as 129 Ola, 129sv, C57BL/6 also may be used for the purpose of making mouse genomic library.

The shuttle vectors of the present invention comprise genomic DNA fragments; those of skill in the art will know various techniques for generating and separating such fragments. For example, purified high-molecular-weight genomic DNA is partially digested with a restriction enzyme such as Sau3A to randomly fragment the DNA and to obtain directly clonable ends. Other enzymes useful for this endeavor will be well known to those of skill in the art. This randomly fragmented DNA is size fractionated through, for example, sucrose density gradient. (Maniatis, T. et al. (1978). The isolation of structural genes from libraries of eukaryotic DNA. Cell 15: 687).

Preferred embodiments disclose a genomic library in which shuttle vectors comprise genomic fragments ranging from about 8 kb to about 13 kb. This is merely an exemplary fragment range and fragments that are larger or smaller than this also may be useful. Preferred embodiments may use shuttle vectors comprising a genomic fragment that is 1 kb, 2 kb, 3 kb, 4 kb, 5 kb, 6 kb, 7 kb, 8 kb, 9 kb, 10 kb, 11 kb, 12 kb, 13 kb, 14 kb, 15 kb, 16 kb, 17 kb, 18 kb or larger. In preferred embodiments, the genomic fragment inserts had an average insert size of 11 kb.

Methods for preparing genomic libraries and cDNA libraries are well known in the art and are described in Sambrook et al., Molecular Cloning, A Laboratory Manual, (section 9, pp. 9.2–9.58 and section 8, pp. 8.2–8.79, respectively) Cold Spring Harbor N.Y. (1989) and in Current Protocols in Molecular Biology, (section 5, pages 5.0.1–5.11.2) Ausubel et al., Eds. John Wiley and Sons Inc. (1987), the relevant sections of which are incorporated herein by reference.

In preferred aspects of the invention, the mouse genomic fragment library in the shuttle vector construct is amplified by transforming it into electrocompetent bacterial cells. The electrocompetent bacterial cells that may be employed in the present invention include but are not limited to eubacteria such as Gram-negative or Gram-positive organisms (e.g., *E. coli* (HB101, DH5a, DH10B and MC1061); Bacilli such as *B. subtilis*; Pseuclomonas species, such as *P. aeruginosa*; Streptomyces spp.; *Salmonella typhimurium*; or *Serratia marcescans*.

In preferred embodiments, the shuttle vectors are transformed into electrocompetent *E. coli*, ElectroMAX DH10B (GIBCO-BRL, Gaithersburg, Md). A portion of each transformation is plated out and 48 individual colonies from each are analyzed for desired size range of inserts and percentage of clones containing inserts.

The amplified DNA and the *E. coli* containing the genomic mouse DNA inserts is organized into a library in which, for example, 1.5 million independent clones generated from the cloning of the shuttle vector comprising the genomic DNA into the bacterial cells are divided into 300 pools of 5000 clones each and plated on 150 mm LB-Amp plates. The *E. coli* colonies are grown overnight and collected by scraping. A portion of each of these pools is saved in, for example, three 96-well microtiter plates and frozen at −70° C. The remainder is processed to obtain DNA, which is also saved in three 96-well microtiter plates. This organization of the library format allows easy identification of pool/s containing gene(s) of interest.

The appropriate pools containing gene or genes of interest from the mouse genomic library are identified by PCR amplification. PCR methods are well known to those of skill in the art and are generally set forth in Sambrook et al., Molecular Cloning: A Laboratory Manual, Cold Spring Harbor Laboratory Press, Cold Spring Harbor, N.Y., (1989); by Ausubel et al., eds Current Protocols in Molecular Biology, Current Protocols Press, (1994).

DNA from either each column of 8 pools or each row of 12 pools from a 96 well plate is combined into a larger pool and assayed by PCR amplification using a pair of primers specific to the gene of interest. Primers are chosen such that they ideally amplify between 0.3 kb to 1.5 kb fragment from the target area in the gene of interest. In designing the primers mouse genomic sequence information of the gene of interest or the information from the human counterpart or closest family member is used as a basis to estimate intron-exon structure of the gene of interest. However, this information is not essential. If genomic structure is neither known nor can be estimated, then primers are chosen based on the cDNA sequence to produce a product within the targeted area of disruption. After identifying positive row(s) or column(s) of combined pools using this PCR step, positive combined pools are analyzed using the same primers to identify the positive individual pool(s). Once the positive pools containing the gene of interest are identified, they are used in homologous recombination to construct a knockout vector.

The inventors have found that successful recombination occurred using pools containing up to 5000 clones. However, a linear decrease in number of recombinants obtained occurred with an increase in pool complexity. A successful recombination event between the gene of interest and the neo/ura cassette depends on several factors. These include transformation efficiency of the host yeast strain, presence of both the genomic clone of interest and the neo/ura cassette within the same yeast cell, and recombination frequency between the two constructs once they are in the same cell.

III. Methods of Making Transgenic Animals

In order to introduce the targeting construct into the germline of an animal, the targeting construct is first introduced into an undifferentiated totipotent cell termed an embryonic stem (ES) cell wherein the construct can recombine with the selected genomic region via their homologous sequences. ES cells are derived from an embryo or blastocyst of the same species as the developing embryo into which they are to be introduced. ES cells are typically selected for their ability to integrate into the inner cell mass and contribute to the germ line of an individual when introduced into the mammal in an embryo at the blastocyst stage of development. Thus, any ES cell line having this capability is suitable for use in the practice of the present invention.

The cells are cultured and prepared for introduction of the targeting construct using methods well known to the skilled artisan. (See, e.g., Robertson, E. J. ed. "Teratocarcinomas and Embryonic Stem Cells, a Practical Approach", IRL Press, Washington D.C. (1987); Bradley et al., *Current Topics in Devel. Biol.* 20:357–371 (1986); by Hogan et al. in "Manipulating the Mouse Embryo": A Laboratory Manual, Cold Spring Harbor Laboratory Press, Cold Spring Harbor, N.Y. (1986); Thomas et al., *Cell*, 51:503 (1987); Koller et al., *Proc. Natl. Acad. Sci. USA*, 88:10730(1991); Dorin et al., *Transgenic Res.*, 1:101 (1992); and Veis et al., *Cell*, 75:229 (1993) all of which are incorporated herein by reference). The targeting construct may be introduced into ES cells by any one of several methods known in the art including electroporation, calcium phosphate co-precipitation, retroviral infection, microinjection, lipofection and other methods. Insertion of the targeting construct into the targeted gene is typically detected by selecting cells for expression of the marker gene contained in the targeting construct which is typically under the control of a promoter which is functional in the target cell type (i.e., promoters which function in embryonic stem cells). ES cells expressing the marker sequence arc then isolated and expanded.

The ES cells having the disruption are then introduced into an early-stage mouse embryo (e.g., blastocyst) (see, e.g., Robertson, supra, Bradley, supra, and Monsour et al., *Nature*, 336:348 (1988)) incorporated herein by reference. Blastocysts and other early stage embryos used for this purpose arc obtained by flushing the uterus of pregnant animals for example, by the methods described in Robertson et al., supra and Bradley et al., supra. The suitable stage of development for the blastocyst is species dependent; however, for mice it is about 3.5 days post-fertilization.

While any embryo of the right age/stage of development is suitable for implantation of the modified ES cell, preferred most embryos are male and have genes coding for a coat color or other phenotypic marker that is different from the coat color or other phenotypic marker encoded by the ES cell genes. In this way, the offspring can be screened easily for the presence of the targeted mutation by looking for mosaic coat color (e.g. agouti) or the other phenotypic markers (indicating that the ES cell was incorporated into the developing embryo). Thus, for example, if the ES cell line carries the genes for white fur, the host embryos selected will preferably carry genes for black or agouti fur.

An alternate method of preparing an embryo containing ES cells that possess the targeting construct is to generate "aggregation chimeras". A morula of the proper developmental stage (about 2½ days post-fertilization for mice) is isolated. The zona pellucida can be removed by treating the morula with a solution of mild acid for about 30 seconds, thereby exposing the "clump" of cells that comprise the morula. Certain types of ES cells such as the R1 cell line for mice can then be co-cultured with the morula cells, forming an aggregation chimera embryo of morila and ES cells, (Joyner, A. L., "Gene Targeting", *The Practical Approach Series*, JRL Press Oxford University Press, New York, 1993, incorporated herein by reference).

A refinement of the aggregation chimera embryo method can be used to generate an embryo comprised of essentially only those ES cells containing the knockout construct. In this technique, a very early stage zygote (e.g., a two-cell stage zygote for mice) is given a mild electric shock. This shock serves to fuse the nuclei of the cells in the zygote thereby generating a single nucleus that has two-fold (or more) the DNA of a naturally occurring zygote of the same developmental stage. These zygotic cells are excluded from the developing embryo proper, and contribute only to forming accessory embryonic structures such as the extra-embryonic membrane. Therefore, when ES cells are co-cultured with the zygotic cells, the developing embryo is comprised exclusively of ES cells, (see Joyner, A. L., supra).

After the ES cells have been incorporated into the aggregation chimera or into the blastocyst, the embryos may be implanted into the uterus of a pseudo pregnant foster mother. While any foster mother may be used, preferred foster mothers are typically selected for their ability to breed and reproduce well, and for their ability to care for their young. Such foster mothers are typically prepared by mating with vasectomized males of the same species. The pseudo pregnant stage of the foster mother is important for successful implantation, and it is species dependent. For mice, this stage is about 2–3 days of pseudopregnancy.

Offspring that are born to the foster mother may be screened initially for mosaic coat color or another phenotypic marker (where the phenotype selection strategy has been employed). In addition, or as an alternative, chromosomal DNA obtained from tail tissue of the offspring may be screened for the presence of the targeted mutation using Southern blots and/or PCR. The offspring that are positive for homologous recombination at the targeted locus will typically be a mosaic of wild-type cells derived from the host embryo and heterozygous cells derived from injected ES cells (i.e., chimeric offspring). Chimeric offspring are crossed with wild-type partners to generate offspring that are heterozygous for the targeted mutations, i.e., all of their cells are heterozygous for the mutation.

Methods for producing transgenic mammals, including rabbits, pigs, and rats, using micro-injection are described in Hamer et al., *Nature* 315:680–683 (1985); U.S. Pat. No. 4,736,866, incorporated herein by reference. Additional methods for producing transgenic animals are generally described by Wagner and Hoppe (U.S. Pat. No. 4,873,191; which is incorporated herein by reference), Brinster et al. 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety). Briefly, this method involves injecting DNA into a fertilized egg, or zygote, and then allowing the egg to develop in a pseudo-pregnant mother. The zygote can be obtained using male and female animals of the same strain or from male and female animals of different strains. The transgenic animal that is born, the founder, is bred to produce more animals with the same DNA insertion. In this method of making transgenic animals, the new DNA typically randomly integrates into the genome by a non-homologous recombination event. One to many thousands of copies of the DNA may integrate at one site in the genome.

Generally, the DNA is injected into one of the pronuclei, usually the larger male pronucleus. The zygotes are then either transferred the same day, or cultured overnight to form 2-cell embryos and then transferred into the oviducts of pseudo-pregnant females. The animals born are screened for the presence of the desired integrated DNA.

DNA clones for microinjection can be prepared by any means known in the art. For example, DNA clones for microinjection can be cleaved with enzymes appropriate for removing the bacterial plasmid sequences, and the DNA fragments electrophoresed on 1% agarose gels in TBE buffer, using standard techniques. The DNA bands are visualized by staining with ethidium bromide, and the band containing the expression sequences is excised. The excised band is then placed in dialysis bags containing 0.3 M sodium acetate, pH 7.0. DNA is electroeluted into the dialysis bags, extracted with a 1:1 phenol:chloroform solution and precipitated by two volumes of ethanol. The DNA is redissolved in 1 ml of low salt buffer (0.2 M NaCl, 20 mM Tris, pH 7.4, and 1 mM EDTA) and purified on an Elutip-D™ column. The column is first primed with 3 ml of high salt buffer (1 M NaCl, 20 mM Tris, pH 7.4, and 1 mM EDTA) followed by washing with 5 ml of low salt buffer. The DNA solutions are passed through the column three times to bind DNA to the column matrix. After one wash with 3 ml of low salt buffer, the DNA is eluted with 0.4 ml high salt buffer and precipitated by two volumes of ethanol. DNA concentrations are measured by absorption at 260 nm in a UV spectrophotometer. For microinjection, DNA concentrations are adjusted to 3 mg/ml in 5 mM Tris, pH 7.4 and 0.1 mM EDTA.

Additional methods for purification of DNA for microinjection are described in Hogan et al. Manipulating the Mouse Embryo (Cold Spring Harbor Laboratory, Cold Spring Harbor, N.Y., 1986), in Palmiter et al. Nature 300:611 (1982); in The Qiagenologist, Application Protocols, 3rd edition, published by Qiagen, Inc., Chatsworth, Calif.; and in Sambrook et al. Molecular Cloning: A Laboratory Manual (Cold Spring Harbor Laboratory, Cold Spring Harbor, N.Y., 1989).

In an exemplary microinjection procedure, female mice six weeks of age are induced to superovulate. The superovulating females are placed with males and allowed to mate. After approximately 21 hours, the mated females are sacrificed and embryos are recovered from excised oviducts and placed in an appropriate buffer, e.g., Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA in a 37.5° C incubator with a humidified atmosphere at 5% $CO_2$, 95% air until the time of injection. Embryos can be implanted at the two-cell stage.

Randomly cycling adult female mice are paired with vasectomized males. C57BL/6 or Swiss mice or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS (Dulbecco's phosphate buffered saline) and in the tip of a transfer pipette (about 10 to 12 embryos). The pipette tip is inserted into the infundibulum and the embryos transferred. After the transfer, the incision is closed by two sutures. The pregnant animals then give birth to the founder animals which are used to establish the transgenic line.

If animals homozygous for the targeted mutation are desired, they can be prepared by crossing animals heterozygous for the targeted mutation. Mammals homozygous for the disruption may be identified by Southern blotting of equivalent amounts of genomic DNA from mammals that are the product of this cross, as well as mammals of the same species that are known heterozygotes, and wild-type mammals. Alternatively, specific restriction fragment length polymorphisms can be detected which co-segregate with the mutant locus. Probes to screen the Southern blots for the presence of the targeting construct in the genomic DNA can be designed as described below.

Other means of identifying and characterizing the offspring having a disrupted gene are also available. For example, Northern blots can be used to probe mRNA obtained from various tissues of the offspring for the presence or absence of transcripts. Differences in the length of the transcripts encoded by the targeted gene can also be detected. In addition, Western blots can be used to assess the level of expression of the targeted gene by probing the Western blot with an antibody against the protein encoded by the targeted gene. Protein for the Western blot may be isolated from tissues where this gene is normally expressed. Finally, in situ analysis (such as fixing the cells and labeling with antibody or nucleic acid probe) and/or FACS (fluorescence activated cell sorting) analysis of various cells from the offspring can be conducted using suitable antibodies to look for the presence or absence of the gene product.

IV. Examples

The present invention is described in more detail with reference to the following non-limiting examples which represent preferred embodiments of the invention. Those of skill in the art will understand that the techniques described in these examples represent techniques described by the inventors to function well in the practice of the invention, and as such constitute preferred modes for the practice thereof. However, it should be appreciated that those of skill in the art should in light of the present disclosure, appreciate that many changes can be made in the specific methods which are disclosed and still obtain a like or similar result without departing from the spirit and scope of the invention.

EXAMPLE 1

Construction of the Shuttle Vector

Figure 4:
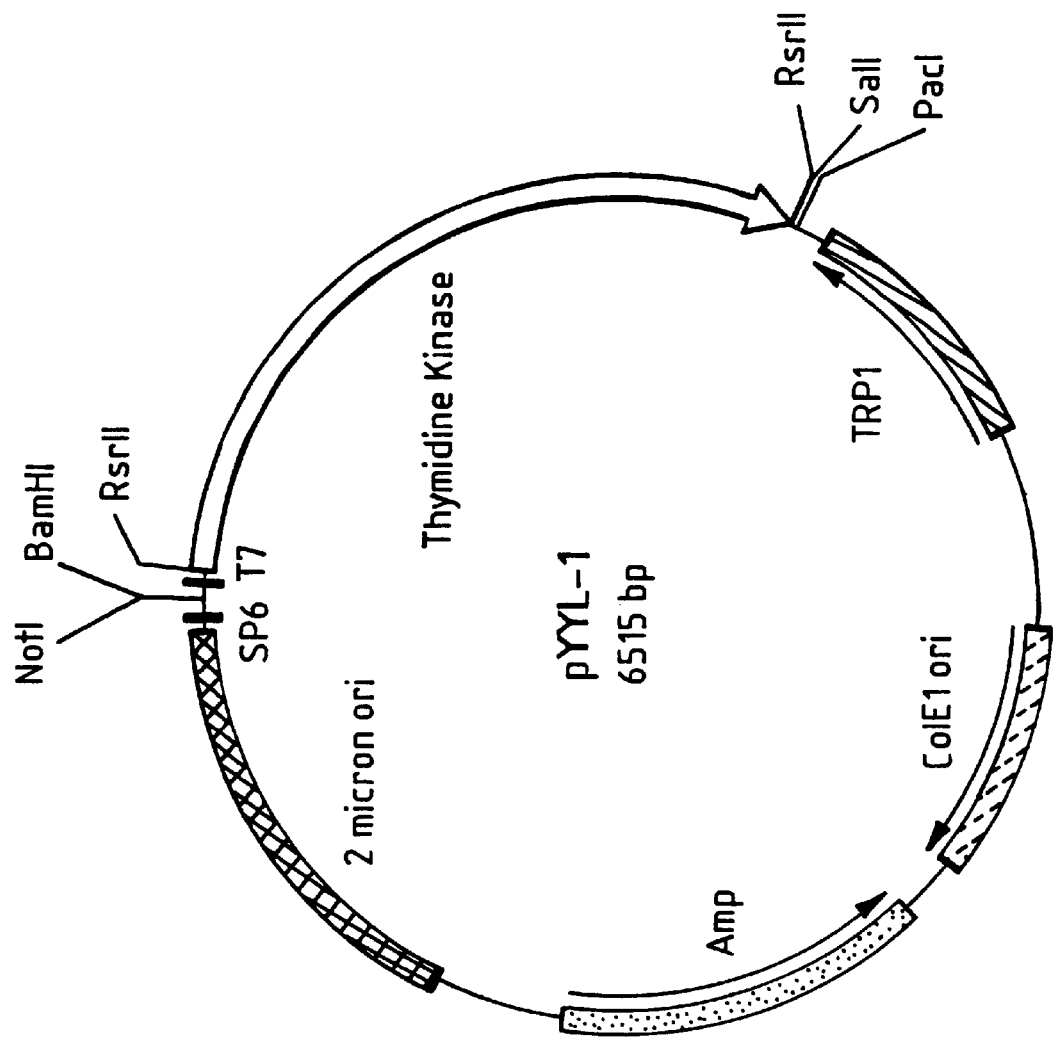
FIG. 4 shows a map of the pYYL-1 mouse knock-out vector.

The present example provides construction and description of the yeast-E. coli shuttle vector pYYL-1 employed in the present invention. (See FIG. 4). The base vector for construction of pYYL-1 was yeast-E-coli shuttle vector pGBT9 (Genbank Accession #U07646) pGBT9 was restriction digested with SphI and the 4.4 kb vector fragment was isolated. Oligonucleotides of SEQ ID NO:1 and SEQ ID NO:2 were annealed and ligated with the 4.4 kb vector fragment at the SphI sites. The annealed oligonucleotide contains SP6 and T7 primer sites and a polylinker containing several unique cloning sites. The resulting ligated vector is named pYYL-1.

SEQ ID NO:1 CAT TTA GGT GAC ACT ATA GCG GCC GCG GAT CCC TAT AGT GAG TCG TAT TAC GGA CCG TCG ACT TAA TTA ACA TG

SEQ ID NO:2 TTA ATT AAG TCG ACG GTC CGT AAT ACG ACT CAC TAT AGG GAT CCG CGG CCG CTA TAG TGT CAC CTA AAT GCA TG

The sequence of the pYYL-1 vector is provided in SEQ ID NO:3. This plasmid is an E. coli-yeast shuttle vector that contains a Bla1 gene (for ampicillin resistance) and ColE1-ORI (replication origin) for maintenance and propagation in E. coli; a 2μorigin of replication and TRP1 gene for propagation in yeast; and TK gene for negative selection in mammalian cells.

The unique BamHl site in this vector is used for inserting the genomic library fragments. The vector was first restriction digested to completion with BamHI to completion and then dephosphorylated using Calf Intestinal Alkaline Phosphtase (New England Biolabs, Beverly, Mass.). Subsequently, Sau3A digested mouse genomic DNA, containing phosphorylated ends, was ligated with the treated vectors. The BamHI site in pYYL-7 site is flanked by Sp6 and T7 priming sequences which can be used in PCR analysis of the inserted fragment in the steps before and after recombination. To facilitate excision of the genomic fragment along with the negative selection marker TK, rare cutting enzyme sites flanking these regions have been engineered into pYYL-1. These sites are NotI on one end and PacI and SalI on the end closer to TK. Of course it should be understood that the rare cutting enzyme sites, markers and flanking sites are only exemplary. Other vectors also may be constructed having alternative replication origins, selection genes and restriction sites, which would be equally useful for the purpose of making mouse genomic libraries and subsequently used in constructing mouse knockout vectors by yeast recombination.

EXAMPLE 2

Construction of the Recombination Cassette

For easy generation of the recombination cassette, the neomycin gene under the PGK promoter and yeast nutritional marker URA3 gene have been cloned in tandem into the pSPORT-1 vector (GIBCO-BRL, Gaithersburg, Md.). A SmaI-HindIII fragment containing the yeast URA3 selection marker was excised from YEP24 plasmid (ATCC#37051) and cloned into pSPORT1 at the corresponding sites. Into this plasmid, an AscI fragment containing the Neomycin gene from pKONeo ( Stratagene, La Jolla, Calif.) was cloned at the Mlu I site. The resultant Neo/Ura3 cassette containing plasmid, pYYL-2, provides the universal template for creating knockout recombinant cassettes for any gene of interest by PCR amplification.

EXAMPLE 3

Construction of Mouse Knock-out Vector for GPR-24 Gene

GPR-24 (also called SLC-1) is a recently discovered G protein-coupled receptor, which is homologous to somatostatin receptors, and binds to the melanin-concentrating hormone (MCH) (Saito et al. 1999. Nature 400:265–269). The coding region of this gene has one 1115 bp intron (intron I).

Two primers (SEQ ID NO:4 and SEQ ID NO:5), which amplified an approximately 2.2 kb fragment spanning the initiating Met and stop codon and contained the intron 1, sequence were used for identification of positive pools of the arrayed mouse genomic library. PCR were performed on DNA from 24 combined pools from three 96-well plates. Each combined pool was comprised of DNA pooled from the 12 wells of each row. The positive pools gave a PCR product of approximately 2.2 kb. PCR amplification was repeated on individual pools comprising two of the positive combined pools. Once the individual positive pools were found, PCR was performed on the positive pools using the gene-specific primers and the vector-specific primers to determine that the desired positive clone had sufficient flanking genomic sequence outside the targeted region of recombination. Each gene specific primer (SEQ ID NO:4 and SEQ ID NO:5) was paired with both vector specific primers, namely Sp6 and T7 (SEQ ID NO:6 and SEQ ID NO:7) to perform the PCR. A positive individual pool that had one long arm of approximately 11.7 kb and a short arm of approximately 1.3 kb flanking the targeted recombination region was used in the next recombination step.

Figure 5:
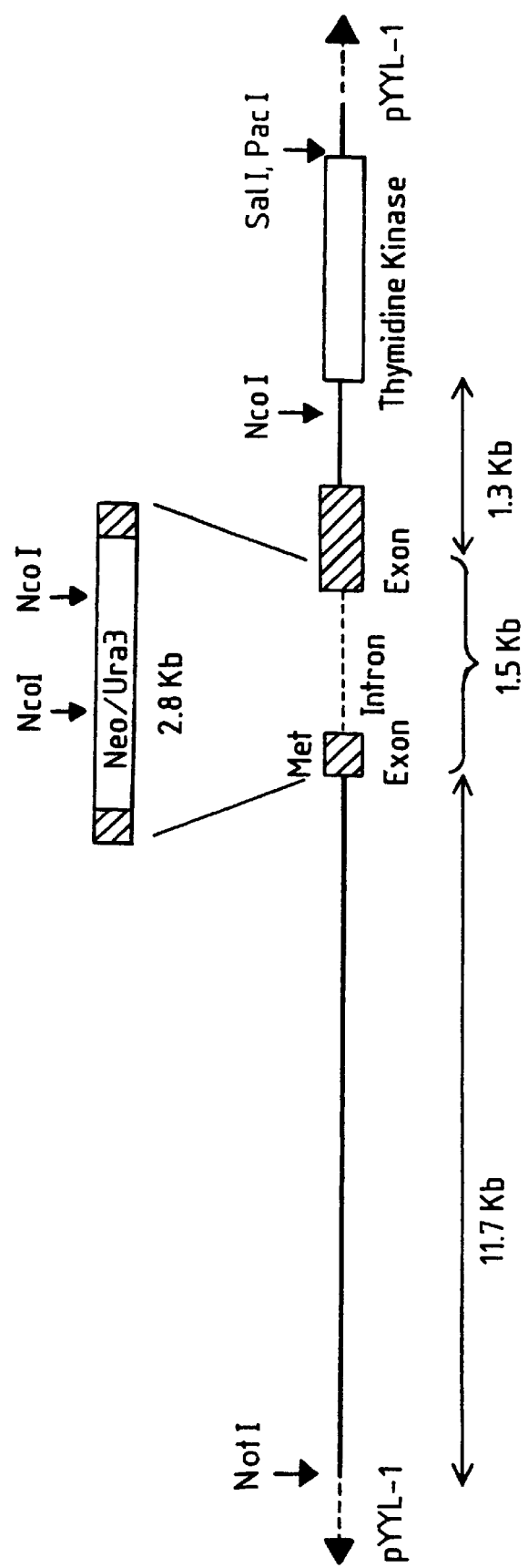
FIG. 5 shows a map of a targeting vector for a GPR24 knock-out.

To generate the recombination cassette, two (sense and antisense) oligonucleotide primers were synthesized of which 45 nucleotides of each were homologous to the targeted area of GPR-24. In addition to the homology to the target region, the sense primer at its 3' end also contains additional 20 bp that correspond to the 5' end of the neomycin gene (SEQ ID NO:8). In the antisense primer 25 bp at the 3' end are homologous to the 3' end of the URA3 gene (SEQ ID NO:9). Using these primers, the recombination cassette for GPR-24 was generated, which included 45-bp flanking sequences at its ends homologous to GPR-24. These primers were designed to delete sequence by recombination from exon I and exon II corresponding to amino terminal 128 amino acids and intron I and replace it with the neo/ura selection cassette (see FIG. 5).

Yeast transformation was performed sequentially. 2.0 μg DNA of the positive pool (in which the desired gene is present in approximately 1:5000 ratio) or from an array in which the positive clone was mixed among other clones in ratios of 1:250, 1:500, and 1:1000 was transformed into yeast and plated onto trp-deficient selective medium. Approximately 20,000 yeast colonies from transformation plates were scraped and the cells were made competent. 100 μl (2 OD$_{600}$ cells) were used to transform 1 μg of cassette DNA. Transformation mixtures were plated on trp- and ura-deficient selective growth medium. In each case, yeast colonies were obtained; however, the number of Trp+Ura+ colonies decreased with the complexity of the pool.

The presence of recombined GPR24 knockout construct in yeast colonies was confirmed by PCR. The gene-specific primer (SEQ ID NO:10) paired with the cassette-specific neo primer (SEQ ID NO:12) and the gene specific primer (SEQ ID NO:11) paired with the cassette-specific ura primer (SEQ ID NO:13), respectively, produced 388 bp and 536 bp fragments, thus confirming homologous recombination at the targeted site. In addition, PCR was performed again to confirm the length and short arms. Positive yeast colonies were grown and plasmids rescued, amplified, and transfected into mouse ES cells.

EXAMPLE 4

Construction of Mouse Knockout Vector for CHL-1 Gene

Figure 6:
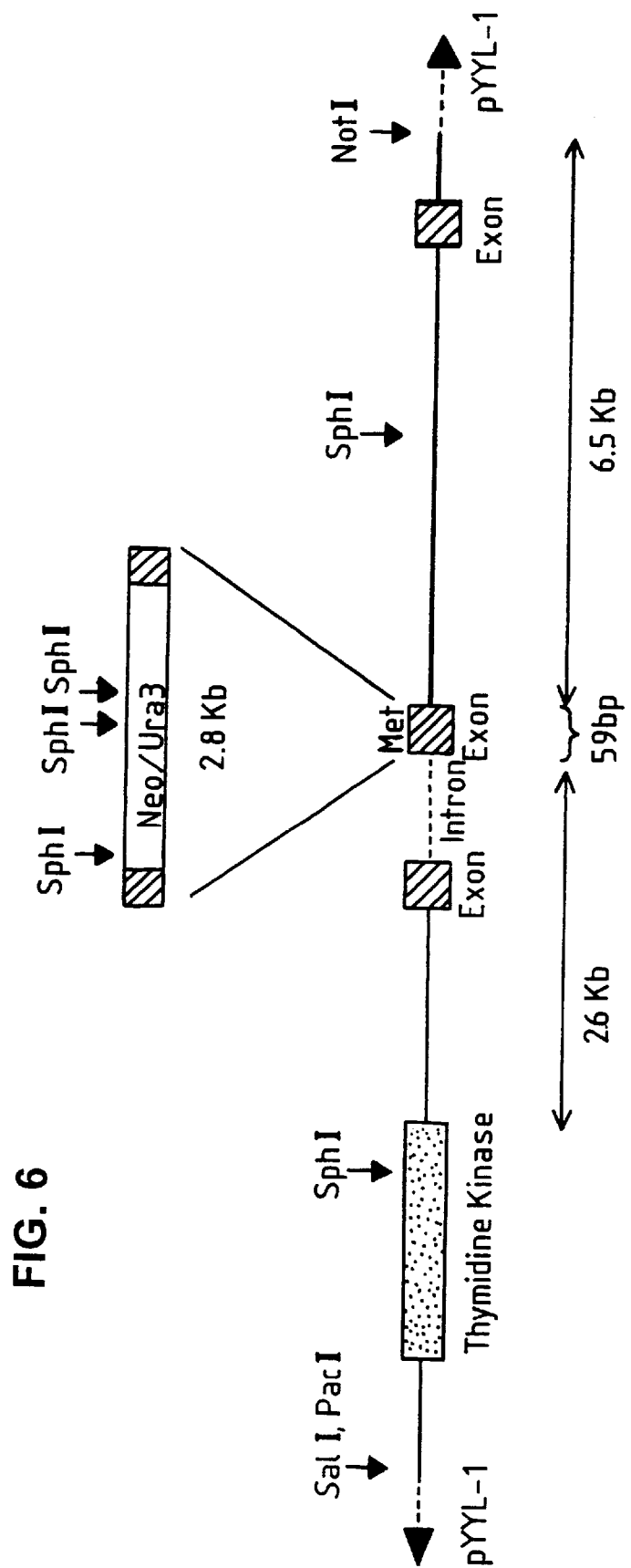
FIG. 6 shows a map of a targeting vector for a CHL-1 knock-out.

CHL-1 is a novel chordin-like secreted molecule. Methods and compositions directed to this gene are disclosed in Ser. No. 60/169,494 filed Dec. 7, 1999 (incorporated herein by reference). The knockout construct for the mouse CHL-1 was constructed as follows: a sense primer specific to signal peptide coding exon (SEQ ID NO:14) and an antisense primer (SEQ ID NO:15) in the adjacent intron downstream of the signal peptide were used to generate a 405-bp PCR product in positive pools. Individual genomic clones of CHL-1 were isolated by colony hybridization. The positive clone that contained an approximately 9.2 kb fragment was used for recombination. The neo/ura cassette flanked with 45 bp CHL-1 specific targeting sequences was generated by PCR amplification using primers of SEQ ID NO:16 and SEQ ID NO:17. The cassette was designed to delete 59 bp from exon I, which includes sequence encoding the initiating methionine and signal peptide (see FIG. 6).

200 ng of the CHL-1 genomic clone DNA and 500 ng of the neo/ura recombination cassette were co-transformed into the yeast competent cells. Under these conditions, 53 yeast colonies grew on trp- and ura-deficient synthetic medium plates. 8 of these colonies were used to confirm recombination of the cassette with the genomic clone by PCR. The gene specific primer (SEQ ID NO:18) paired with the cassette specific neo primer (SEQ ID NO:12) and the gene-specific primer (SEQ ID NO:19) paired with the cassette-specific ura primer (SEQ ID NO:13), respectively produced 500-bp and 693-bp fragments, which indicated successful recombination. The plasmid-specific primers Sp6 or T7 were used in combination with the cassette-specific neo or ura primers to estimate length of flanking genomic sequences to the neo/ura cassette. The analysis showed that the long arm was approximately 6.6 kb and the short arm was approximately 2.5 kb. Plasmids were rescued and processed as described above for GPR24.

While the methods and compositions herein have been described in terms of preferred embodiments, it will be apparent that variations may be applied to the methods and/or compositions without departing, from the concept, spirit and scope of the invention. More specifically, it will be apparent that assays which are physiologically related may be substituted for the assays described herein while still producing the same or similar results. All such similar substitutes and modifications apparent to those of skill in the art are deemed to be within the scope of the invention as defined by the appended claims.

To the extent that certain exemplary procedural or other details supplementary to those described herein may be found in the references cited herein, such references are all specifically incorporated herein by reference.

I claim:

1. A method of preparing a genomic library for use in producing knockout targeting vectors comprising:
   a) preparing genomic DNA fragments of pre-selected sizes wherein said genomic DNA comprises mouse genomic DNA fragments ranging from 8 kb to 14 kb;
   b) preparing a shuttle vector comprising inserting said genomic DNA fragments into a yeast vector wherein said yeast vector is pYYL-1, which comprises:
      i) a bacterial origin of replication;
      ii) a bacterial selection marker;
      iii) a yeast origin of replication;
      iv) a yeast selection marker; and
      v) a selectable marker for selection of mammalian cells;
   c) introducing said vector into bacterial host cells to amplify said shuttle vectors in transformed bacterial host cells; and;
   d) arraying said transformed bacterial host cells into pools wherein the bacterial host cells comprise said shuttle vectors and wherein said pools comprise genomic fragments of pre-selected sizes
      wherein said pYYL-1 vector comprises a 4.4 kb fragment, generated through a SphI restriction digestion of yeast-*E. coli* shuttle vector pGBT9, wherein said 4.4 kb fragment is annealed at the SphI sites to a first oligonucleotide containing a SP6 site and a second oligonucleotide containing a T7 site.

2. The method of claim 1, wherein said mouse genomic DNA fragments are isolated from a mouse strain selected from the group consisting of 129svj, 129 Ola, 129sv, and C57BL/6.

3. The method of claim 1, wherein said genomic fragments of step (a) generate between $3 \times 10^6$ and $5 \times 10^6$ clones.

4. The method of claim 1, wherein said host cells are bacterial cells selected from the group consisting of *Escherichia coli, Bacillus subtilis, Pseudomonas aeruginosa, Salmonella typhiniurium* and *Serratia marcescans*.

5. The method of claim 4, wherein said host cell is *E. coli*.

6. The method of claim 1, wherein said bacterial origin of replication is selected from the group consisting of ColE1-ORI, F and R1 bacterial origin of replication.

7. The method of claim 1, wherein said bacterial origin of replication is an *E. coli* origin of replication.

8. The method of claim 7, wherein said *E. coli* origin of replication is ColE1-ORI.

9. The method of claim 1, wherein said yeast origin of replication is selected from the group consisting of Cen, 2μ and the autonomous replication sequence.

10. The method of claim 1, wherein said marker for bacterial propagation is selected from the group consisting of ampicillin resistance, tetracycline resistance, neomycin resistance, kanamycin resistance and chloramphenicol resistance.

11. The method of claim 10, wherein said marker for ampicillin resistance is BlaI.

12. The method of claim 1, wherein said marker for propagation in yeast is selected from the group consisting of trp1, His, Ura3, Arg, Ade and Leu2.

13. The method of claim 1, wherein said selectable marker for mammalian cells is selected from the group consisting of neomycin resistance, hygromycin resistance, zeocin resistance, Salmonella HisD and puromycin-acetyl transferase.

14. The method of claim 1, further comprising a negative selectable marker.

15. The method of claim 14, wherein said negative selectable marker is a negative selectable marker for mammalian cells and is selected from the group consisting of thymidine kinase and xanthine-guanine-phosphoribosyltransferase.

16. The method of claim 1, wherein said yeast vector further comprises a BamHI site for inserting said genomic fragments.

17. The method of claim 16, wherein said BamHI site is flanked by SP6 and T7 priming sequences to facilitate PCR amplification.

18. The method of claim 1, wherein said shuttle vector further comprises rare cutting enzyme sites selected from the group consisting of NotI PacI and SalI flanking the genomic fragment.

19. The method of claim 15, wherein said shuttle vector comprises rare cutting restriction enzyme sites selected from the group consisting of NotI PacI and SalI flanking the mammalian selection marker.

20. A genomic library prepared according to the method of claim 1.

21. A method of preparing a genomic library comprising:
   a) preparing size selected genomic DNA ranging from 8 kb to 14 kb in size;
   b) preparing a shuttle vector comprising said genomic DNA and a the pYYL-1 yeast vector, wherein said pYYL-1 vector comprises a 4.4. kb fragment, generated through a SphI restriction digestion of yeast-*E. coli* shuttle vector pGBT9, wherein said 4.4 kb fragment is annealed at the SphI sites to a first oligonucleotide containing a SP6 site and a second oligonucleotide containing a T7 site;
   c) amplifying said shuttle vector in transformed bacterial host cells; and
   d) arraying said transformed bacterial host cells into pools wherein the bacterial host cells comprise said shuttle vectors and wherein said pools comprise a library of genomic fragments of pre-selected sizes.

22. A genomic library prepared according to the method of claim 21.

23. The genomic library of claim 22, wherein said library is a mammalian genomic library.

24. The genomic library of claim 23, wherein said mammalian genomic library is a mouse genomic library.

* * * * *

UNITED STATES PATENT AND TRADEMARK OFFICE
CERTIFICATE OF CORRECTION

PATENT NO. : 6,503,712 B1
DATED : January 7, 2003
INVENTOR(S) : Sushil K. Thukral It is certified that error appears in the above-identified patent and that said Letters Patent is hereby corrected as shown below:

Title page, Item [54] and Column 7, lines 1-3,
Replace "METHODS AND COMPOSITIONS FOR PREPARING A GENOMIC LIBRARY FOR KNOCKOUT TARGETING VECTORS" with -- HIGH THROUGHPUT KNOCKOUT CONSTRUCTS IN YEAST BY HOMOLOGOUS RECOMBINATION --

Column 33,
Line 45, replace "step (a)" with -- step (c) --
Line 59-60, replace "Cen, $2\mu$and" with -- Cen, $2\mu$ and --

Signed and Sealed this

Twelfth Day of August, 2003

JAMES E. ROGAN
*Director of the United States Patent and Trademark Office*